(12) United States Patent
Zenhausern et al.

(10) Patent No.: US 12,233,408 B2
(45) Date of Patent: Feb. 25, 2025

(54) SMART STORAGE CONTAINER FOR HEALTH LOGISTICS

(71) Applicants: Arizona Board of Regents on Behalf of the University of Arizona, Tucson, AZ (US); The Trustees of Columbia University in the City of New York, New York, NY (US)

(72) Inventors: Frederic Zenhausern, Phoenix, AZ (US); Brett Duane, Phoenix, AZ (US); Jian Gu, Phoenix, AZ (US); Alan Nordquist, Phoenix, AZ (US); David Brenner, New York, NY (US); Mikhail Repin, New York, NY (US)

(73) Assignees: Arizona Board of Regents on Behalf of the University of Arizona, Tucson, AZ (US); The Trustees of Columbia University in the City of New York, New York, NY (US)

( * ) Notice: Subject to any disclaimer, the term of this patent is extended or adjusted under 35 U.S.C. 154(b) by 895 days.

(21) Appl. No.: 17/293,707

(22) PCT Filed: Dec. 5, 2019

(86) PCT No.: PCT/US2019/064737
§ 371 (c)(1),
(2) Date: May 13, 2021

(87) PCT Pub. No.: WO2020/118085
PCT Pub. Date: Jun. 11, 2020

(65) Prior Publication Data
US 2022/0001378 A1 Jan. 6, 2022

Related U.S. Application Data

(60) Provisional application No. 62/775,693, filed on Dec. 5, 2018, provisional application No. 62/775,507, filed on Dec. 5, 2018.

(51) Int. Cl.
*B01L 3/00* (2006.01)
*C12N 1/04* (2006.01)
*G01N 33/48* (2006.01)

(52) U.S. Cl.
CPC ........... *B01L 3/50* (2013.01); *B01L 2200/185* (2013.01); *B01L 2300/021* (2013.01);
(Continued)

(58) Field of Classification Search
CPC ......... B01L 2200/147; B01L 2200/185; B01L 2300/021; B01L 2300/023;
(Continued)

(56) References Cited

U.S. PATENT DOCUMENTS 6,020,575 A  2/2000  Nagle et al.
6,584,797 B1  7/2003  Smith et al.
(Continued)

FOREIGN PATENT DOCUMENTS

WO  2016/147018 A1  9/2016
WO  2019/210195 A1  10/2019
(Continued)

OTHER PUBLICATIONS

Chasteen (2013) "Challenges in Managing the Cold Chain," BioPharm International—Nov. 1, 2013, 26(11): 40-45. Accessed from: http://www.biopharminternational.com/challenges-managing-cold-chain-0.
(Continued)

*Primary Examiner* — Jennifer Wecker
(74) *Attorney, Agent, or Firm* — Leydig, Voit & Mayer, Ltd.

(57) ABSTRACT

Provided herein are methods and related devices for pre-processing a biological sample during transit. The method may comprise the steps of: storing a biological sample in a storage container having walls that defines a storage volume;
(Continued)

transporting the storage container with the stored biological sample to a sample processing facility; controlling one or more storage container parameters during the transporting step to initiate preprocessing of the biological sample; wherein the controlling step improves a processing parameter at the sample processing facility.

19 Claims, 23 Drawing Sheets

(52) U.S. Cl.
CPC . *B01L 2300/023* (2013.01); *B01L 2300/0663* (2013.01); *B01L 2300/18* (2013.01); *C12N 1/04* (2013.01); *G01N 33/48* (2013.01)

(58) Field of Classification Search
CPC ......... B01L 2300/0663; B01L 2300/18; B01L 2300/1827; B01L 3/50; B01L 7/00; B01L 7/04; C12N 1/04; G16H 10/40; G01N 33/48
See application file for complete search history.

(56) References Cited

U.S. PATENT DOCUMENTS

| | | | |
|---|---|---|---|
| 10,898,896 B2 | 1/2021 | Zenhausern et al. | |
| 11,221,966 B2 | 1/2022 | Zenhausern et al. | |
| 2003/0087423 A1 | 5/2003 | Haywood et al. | |
| 2004/0226309 A1 | 11/2004 | Broussard | |
| 2008/0212643 A1* | 9/2008 | McGahhey | B01L 7/52 374/E1.004 |
| 2012/0082985 A1* | 4/2012 | Zenhausern | C12Q 1/686 204/603 |
| 2013/0183747 A1 | 7/2013 | Fukuda et al. | |
| 2014/0248621 A1 | 9/2014 | Collins | |
| 2014/0370608 A1* | 12/2014 | Gelbman | G01N 35/00584 422/67 |
| 2015/0017627 A1 | 1/2015 | Anderson et al. | |
| 2016/0363605 A1* | 12/2016 | Liepold | F24F 3/167 |
| 2017/0023546 A1 | 1/2017 | Holmes et al. | |
| 2017/0072393 A1 | 3/2017 | Jackson et al. | |
| 2017/0082585 A1* | 3/2017 | DeWitte | H01J 49/0031 |
| 2019/0345431 A1 | 11/2019 | Barrett et al. | |
| 2020/0056140 A1* | 2/2020 | Afshar | C12M 41/48 |
| 2020/0197930 A1* | 6/2020 | Higgins | B01L 7/525 |
| 2021/0030347 A1 | 2/2021 | Zenhausern et al. | |
| 2021/0079337 A1 | 3/2021 | Zenhausern et al. | |
| 2021/0199651 A1 | 7/2021 | Zenhausern et al. | |

FOREIGN PATENT DOCUMENTS

| | | |
|---|---|---|
| WO | 2020/264385 A1 | 12/2020 |
| WO | 2020/264388 A1 | 12/2020 |

OTHER PUBLICATIONS

Gibson (Feb. 2, 2012) "Business Trends in Shipping Logistics for Medical Equipment," MDDI. Accessed from: https://www.mddionline.com/business-trends-shipping-logistics-medical-equipment.

Health Products Regulatory Authority (Oct. 2020) "Guide to Control and Monitoring of Storage and Transportation Temperature Conditions for Medicinal Products and Active Substances," IA-G0011-3, 20 pp.

International Preliminary Report on Patentability mailed Jun. 17, 2021 in International application No. PCT/US2019/064737, 9 pp.

Markmann (Dec. 2016) "Pushing the Limits of Temperature Control," World Courier. Accessed from: https://www.worldcourier.com/insights/pushing-the-limits-of-temperature-control.

O'Donnell (Jan. 2014) "Temperature-controlled transport operations, Technical supplement to WHO Technical Report Series, No. 961, 2011" WHO Press, World Health Organization, 29 pp.

Sykes (Mar. 2018) "Time- and Temperature-Controlled Transport: Supply Chain Challenges and Solutions," Pharmacy & Therapeutics, 43(3): 154-157, 170. Accessed from: https://www.ncbi.nlm.nih.gov/pmc/articles/PMC5821242/.

World Courier (Jun. 2017) "The Move from Cold-Chain to Temperature-Controlled Shipping," https://www.outsourcing-pharma.com/Headlines/Promotional-Features/Temperature-controlled-pharmaceutical-logistics.

* cited by examiner

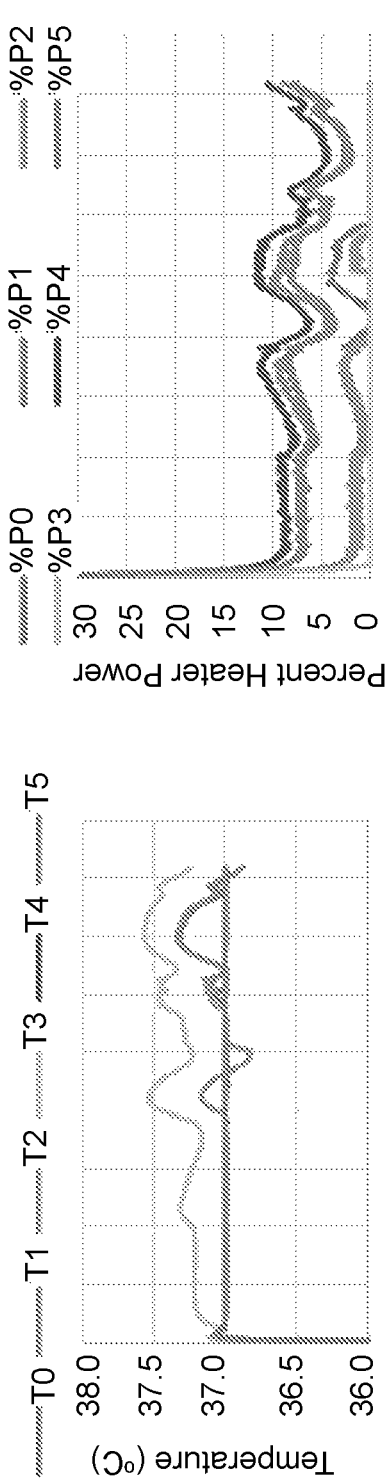
FIG. 15
FIG. 16
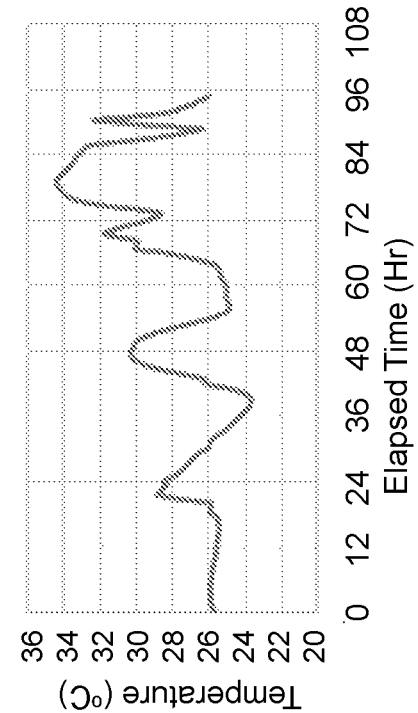
FIG. 18
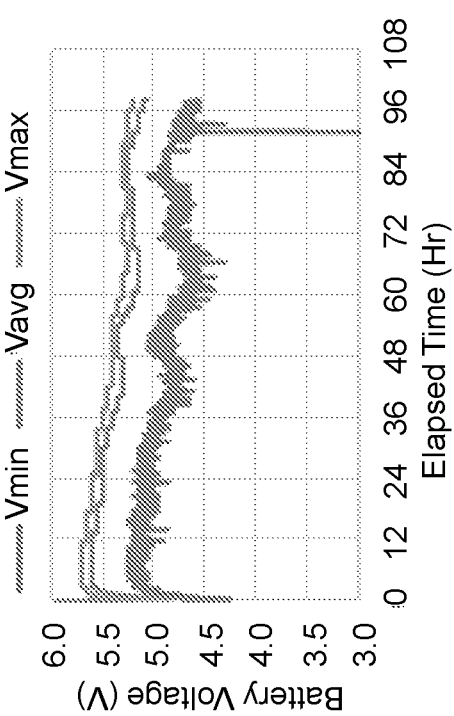
FIG. 17

SMART STORAGE CONTAINER FOR HEALTH LOGISTICS

CROSS-REFERENCE TO RELATED APPLICATIONS

This patent application is a U.S. National Stage Application filed under 35 U.S.C. § 371 of International Application No. PCT/US2019/064737 filed Dec. 5, 2019, which claims the benefit of U.S. Provisional Patent Application Nos. 62/775,693 and 62/775,507, each filed Dec. 5, 2018, which are specifically incorporated herein.

STATEMENT REGARDING FEDERALLY SPONSORED RESEARCH OR DEVELOPMENT

This invention was made with government support under Grant Nos. AI067773 and AG058852, awarded by National Institutes of Health and Grant No. W81XWH-15-2-0076, awarded by ARMY/MRDC. The government has certain rights in the invention.

BACKGROUND

There is an expanding market for transportation of critical medical products and there is a need for a cost effective and efficient way to transport the products without spoilage. Although commercial transportation services are available, even through large companies, there is still a need for greater efficiency, control and decreased transportation cost, particularly of biological samples where time-to-diagnosis is of importance.

Although conventional shipping packaging can provide storage of medical products to preserve their integrity, (often by thermal isolation and cooling), this refrigeration adds cost and complex logistical components while restricting access to the biospecimen or medical product for any active processing or inspection. Such simple storage-type control, however, does not address the need in the art for reliable control of various parameters that can control any number of parameters that would be useful in readying a sample contained in the box for subsequent handling, processing, analyzing and/or testing.

For example, there is a need in the art to address certain operational scenarios that may require pre-processing and monitoring of biological samples during transportation to optimize the emergency response. Such applications often require remote thermal and sensor actuation. Provided herein is an "on-demand thermal actuated shipping box technology" which allows commercially available insulated-based (e.g. foam, vacuum-insulated-panel) shipping boxes to be equipped with low cost electronic circuitry panels to enable active control of the temperature of the inside volume of the box where medical and biological products can be stored and provide remote monitoring during the shipment cycle. Multiple functionalities for precisely monitoring temperature, humidity, moisture, GPS tracking, and other sensing can be communicated and continuously recorded by conventional communication network systems. More specific diagnostic bio-activation of the products, such as DNA extraction, specimen mixing with reagents during transport including at well-controlled temperatures that may actively increase and decrease depending on the process step, provides the ability to take advantage of the otherwise wasted down-time associated with sample transport.

SUMMARY

The invention provides a smart container for storing of samples that have been collected at one site and that are being sent to another site for processing, including for processing used to provide a diagnostic or therapeutic purpose. The containers provide a number of functional benefits, including the ability to preprocess the sample, with the preprocessing intimately tied to the transportation step and the particular sample processing facility. In this manner, sample integrity may be maintained, and the sample may be automatically tailored to, and be made ready for, the sample processing facility, thereby decreasing processing time at the facility and/or increasing sample fidelity and resultant diagnosis integrity by the facility.

Provided herein are devices and related methods related to supply chain strategy which addresses the need for efficient delivery of non-refrigerated essential medicines and other critical medical products (e.g. rapid diagnostics, disinfectants) or transportation of biospecimen during which these are undergoing some analytical pre-processing (e.g. blood cell culture) while being shipped. The strategy incorporates a smart shipping box with low cost electronic monitoring panels for controlled environmental conditions to ensure integrity of health products during logistical transportation (e.g. constant room temperature (CRT) storage stability) or distribution and medical countermeasures to support critical public health needs through pre-processing of biological specimens during rapid epidemic or disaster response, but also for standard clinical laboratory preparation or on-demand logistics in healthcare. Conventional transportation but also emerging autonomous systems are also suitable for implementing the present invention.

Provided are methods of preprocessing a biological sample during transit. The method may comprise the steps of: storing a biological sample in a biological storage container having walls that defines a storage volume; transporting the storage container with the stored biological sample to a sample processing facility; controlling one or more storage container parameters during the transporting step to initiate preprocessing of the biological sample; wherein the controlling step improves a processing parameter at the sample processing facility. Of course, the invention is compatible with non-biological samples, with non-biological samples capable of being stored in a storage container. Basically, any material that is being shipped off-site to a processing facility may be utilized herein, so long as there is a preprocessing step that can be moved from the processing facility to the storage container in transit. This may involve specific chemical application, incubation, temperature cycling, physical separation (e.g., electric and/or magnetic fields, centrifugation) and the like.

Also provided is a device for carrying out any of the methods described herein. For example, the device may be a cylinder-shaped or box-shape storage container, with any of the components described herein incorporated with or connected to the container.

The storage container may comprise one side-wall or a plurality of interconnected side-walls, each side-wall having a top edge and a bottom edge, a top wall; a bottom wall, wherein the top wall connects a top edge of each of the side walls and the bottom wall connects a bottom edge of each of the side walls, thereby forming a storage volume formed by inner surfaces of the side-walls, top wall and bottom wall; one or more temperature sensors connected to each of the wall inner surfaces; a thermal actuator connected to each of the wall inner surfaces; optionally at least one additional temperature sensor positioned to measure a storage volume temperature or an environmental temperature in a region adjacent to an outer surface of the walls; a position sensor, such as a position (GPS) sensor connected to at least one of the walls or otherwise reliably positioned within a box wall or storage volume; a wireless transmitter and/or receiver for wirelessly transmitting data to, and/or receiving instructions from, an external controller; wherein the storage volume is configured to receive a temperature-sensitive cargo for transport and the thermal actuators provide a time-varying steady state temperature during transport.

The wall preferably has a thermally-conductive inner surface to facilitate temperature uniformity across the inner surface. As used herein, "temperature uniformity" refers to a steady-state condition wherein the maximum deviation from average temperature is less than or equal to 10° C., less than or equal to 1° C., or less than or equal to 0.1° C.

Beyond the inner surface, the remaining bulk of the wall preferably comprises thermal insulators and/or heat storage materials to isolate the surrounding environmental temperature from the internal temperature corresponding to the storage volume. In this manner, the internal temperature is reliably controlled, irrespective of external environmental temperature.

Any of storage container walls may comprise multiple layers, such as thermal conductive inner surface layers and multiple layers of thermal insulating materials and heat storage materials. Examples of layers that may be used in the walls include thermal conductive layers that are one or more of: thin metal layers such as copper, aluminum, or composite structures, such as printed circuit board with thin conductive (e.g., copper) layers on support layers, or composite structures with electrically conductive wires distributed on a support substrate. The surface can be rigid or flexible. Examples of thermal insulating layers include Styrofoam, vacuum-insulated-panel. Examples of the heat storage materials include water and other phase change materials (PCMs). The PCMs are also known as latent heat storage materials, and can comprise an organic material, salt hydrates, or other types. The PCMs may have a phase change corresponding to a solid to liquid/liquid to solid or a solid-solid phase change, such as a change in crystalline structure. During the phase change, energy is released/absorbed, thereby providing a convenient means for storing and releasing large amounts of energy for reliable cooling and heating. Examples of PCMs include sodium sulfate, lauric acid, Trimethylolethane, paraffin, Manganese(II) nitrate, and the like. Water, even without phase change, can store and release large amounts of energy due to its high specific heat to serve as a good heat storage material.

As used herein, "actuator" refers to a device that can effect a change in a physical parameter, such as a thermal actuator, humidifier, centripetal force, and the like. Such actuation of actuator may be effected by a controller with heating and thermal feedback circuit elements on each wall panel that are controlled by the controller. Optionally, the controller may be positioned on the top panel. A thermal actuator may be positioned on an inner-facing surface, such as a thermally-conductive surface, or may be incorporated within the inner-facing surface.

The bulk of the wall is configured to minimize the impact of the surrounding environment temperature, such as by insulation layers (e.g., foam or vacuum-insulated-panel(s) with low thermal conductivity) and/or by large heat storage layers (e.g., formed by water or other PCMs). The container walls are compatible with composite wall structures, such as insulation/heat storage/insulation multilayers, with an inner surface formed of a thermally-conductive layer to facilitate uniform inner surface temperatures. Use of temperature sensors can facilitate temperature control in an automated-feedback loop.

The container surface is compatible with any number of thermal actuation mechanisms, including resistive, thermos-electric and/or electromagnetic.

The devices and methods provided herein may have a battery pack to provide energy to the system operation. Examples of other components inside the storage volume include to facilitate other non-thermal pre-processing, such as a centrifuge system for liquid dispensing during transportation.

Any of the methods and devices provided herein may relate to precise temperature control, including over wide temperature ranges. For example, a biological sample may be stored at cold, even below freezing temperatures. During processing, such as PCR, the temperature may be controlled at relatively high temperatures, such as above the temperature of DNA strand separation (e.g., about 95° C.). Accordingly, temperature sensors and thermal actuators may be used to provide a temperature control ranging from below or about 0° C. to about 100° C., or between 1° C. and 100° C., and sub-ranges thereof, such as appropriate for thermal cycling for PCR amplification, and at physiological ranges suitable for cell culture, such as between about 35° C. and 39° C., or about 37° C. Accordingly, the methods and devices accommodate a steady-state control of temperature within about plus/minus 5° C., 1° C., or 0.1° C., and specific control of the magnitude of steady state temperature, including at higher temperatures (greater than 90° C.), intermediate annealing (in the range of 40° C. to 90° C.), physiological range (around 37° C.) and in a storage range (less than 5° C.), and switching among any such steady-state regimes.

The temperature sensors and actuators may be arranged so as to achieve a desired spatial density, with a certain number of sensors and actuators per area (e.g., $N/cm^2$). For example, the temperature sensor density may be between about 1 sensor/10 $cm^2$ to 1 sensor/100 10 $cm^2$, and any subranges thereof. Thermal actuators may be paired with the temperature sensors, so that there is a type of feedback control of temperature, with the temperature sensor reading the temperature and the actuator controlled by the output of the temperature sensor, so as to maintain a desired temperature in the storage volume. In this manner, certain actuators may be on, others off, and still others providing a cooling action, so as to maintain a steady-state temperature throughout the storage volume. This may occur, for example, with a storage container supported by a cold surface, with an opposing surface exposed to a hot light or sunlight.

One advantage of the methods and devices provided herein is that they can be configured to be used with any of a wide range of transport platforms. For example, the devices can be scaled to be compatible with drone technology, such as being picked-up, transported and/or delivered. In this manner, the smart storage container can be configured to have a certain size and mass compatible with an aerial drone, such as less than 500 pounds for high-end professional drones, down to less than 20 or 10 pounds for hobby-type drones.

Representative embodiments of the invention include, but are not limited to, any of:

1: A method of preprocessing a biological sample during transit, the method comprising the steps of: storing a biological sample in a storage container having walls that define a storage volume; transporting the storage container with the stored biological sample to a sample processing facility; controlling one or more storage container parameters during the transporting step to initiate preprocessing of the biological sample; wherein the controlling step improves a biological sample processing parameter at the sample processing facility.
2. The method of embodiment 1, wherein the improved biological sample processing parameter is one or more of: a decrease in a number of processing steps at the sample processing facility; a decrease in a processing time required at the sample processing facility upon delivery of the biological sample to the sample processing facility; or an improved integrity of the sample processing outcome.
3. The method of embodiment 1, further comprising the step of sensing a storage container parameter during the transporting step with one or more sensors.
4. The method of any of embodiments 1-3, further comprising the step of collecting the biological sample, wherein the biological sample comprises a body fluid sample, a tissue sample, or an environmental sample.
5. The method of any of embodiments 1-4, wherein the biological sample is used in an assay selected from the group consisting of: a radiological exposure assay; a cancer assay; a chemical assay; a biothreat exposure assay; a diagnostic assay; a molecular imaging assay; and a spectroscopic assay.
6. The method of any of embodiments 1-5, wherein the one or more controlled storage container parameters is one or more of: temperature, reagent introduction, fixative introduction, centrifugation, mixing, washing, isolation, separation of one or more sample constituents, liquid manipulation, gas manipulation, or environmental control.
7. The method of any of embodiments 1-6, wherein the preprocessing comprises culturing of cells in the biological sample.
8. The method of any of embodiments 1-7, wherein the controlled storage container parameters vary over time during the transporting step.
9. The method of any of embodiments 1-8, wherein the storage container is vacuum-insulated comprising a plurality of sensors and actuators for controlling temperature in the storage container.
10. The method of any of embodiments 1-9, wherein the storage container comprises a plurality of sensors selected from the group consisting of: a temperature sensor, an accelerometer; a position (GPS) sensor, a time sensor, a humidity sensor, a mechanical shock sensor, a tilt sensor, a radiation sensor, an optical sensor, a magnetic sensor, and any combinations thereof.
11. The method of any of embodiments 1-10, wherein the storage container comprises a plurality of actuators selected from the group consisting of: a thermal actuator, a fluidic actuator, a mechanical actuator, an optical actuator, an electronic actuator, and any combinations thereof.
12. The method of any of embodiments 1-11, wherein the storage container walls correspond to six surfaces, wherein a thermal actuator and a temperature sensor is connected to each surface, and a tethered temperature sensor is connected to the storage container to measure a container volume temperature or an external environmental temperature.
13. The method of any of embodiments 1-12, wherein the storage container comprises temperature sensors and thermal actuators that provide a steady-state temperature control of between 1° C. and 100° C. with a steady state temperature deviation that is within ±0.5° C. of a selected steady-state temperature over the transporting step, including a user-selected time-varying steady-state temperature.
14. The method of any of embodiments 1-13, wherein the storage container comprises an energy source, optionally a primary cell and/or a secondary cell, to provide power and control of the one or more storage container parameters for a time period that is greater than 0.25 hours and less than 7 days.
15. The method of any of embodiments 1-14, wherein the storage container further comprises a wireless transmitter and a receiver for two-way communication with an external controller, wherein the external controller is optionally a hand-held device or a computer.
16. The method of embodiment 15, further comprising the step of remotely controlling the one or more storage container parameters by sending from the external controller a control signal to the actuators.
17. The method of any of embodiments 1-16, further comprising the step of recording a time course of system parameters, wherein the system parameters are selected from the group consisting of storage container location, storage container orientation, an impact force on the storage container, thermal actuator power level, temperature sensor reading, and any combinations thereof.
18. The method of any of embodiments 1-17, wherein each of a plurality of thermal actuators are independently controlled to accommodate a spatially-varying thermal load over an external surface of the storage container.
19. The method of any of embodiments 1-18, further comprising the step of automatically actuating the thermal actuators to maintain the container volume within a user-specified temperature range.
20. The method of any of embodiments 1-19, further comprising monitoring an operation parameter selected from the group consisting of: main battery voltage, power disconnect event due to impact, thermal actuator disabled due to battery depletion, and internal error.
21. A storage container comprising: one side-wall or a plurality of interconnected side-walls, each side-wall having a top edge and a bottom edge, a top wall; a bottom wall, wherein the top wall connects a top edge of each of the side walls and the bottom wall connects a bottom edge of each of the side walls, thereby forming a storage volume formed by inner surfaces of the side-walls, top wall and bottom wall; a temperature sensor connected to each of the wall inner surfaces; a thermal actuator connected to each of the wall inner surfaces; optionally at least one additional temperature sensor positioned to measure a storage volume temperature or an environmental temperature in a region adjacent to an outer surface of the walls; a position sensor connected to at least one of the walls; a wireless transmitter and/or receiver for wirelessly transmitting data to, and/or receiving instructions from, an external controller; wherein the storage volume is configured to receive a temperature-sensitive cargo for transport and the thermal actuators provide a time-varying steady state temperature during transport.
22. The method of any of embodiments 1-20, wherein the transporting step comprises transporting the storage container by an aerial drone. This is accomplished by scaling down the storage container so that it is compatible for transport by a drone.

BRIEF DESCRIPTION OF THE SEVERAL VIEWS OF THE DRAWING(S)

FIGS. 1A-1D Temperature-controlled shipping container.
FIG. 1A is a six-sided shipping container with four side walls. FIG. 1B is a three-sided shipping container with one side wall. FIG. 1C is a top-down view of a shipping container to illustrate the cargo and various components, including sensors, actuators and transmission electronics. FIG. 1D is a photograph of the shipping container, with the top lid opened, to illustrate various circuitry. FIG. 1E illustrates the multilayer-wall configuration, with a PCM and an actuator to generate heat via resistive heating.

FIG. 2 Plot of external temperature (° C.) as a function of time.

FIG. 3 Plot of each of the panel temperature (° C.) (measured with temperature sensors labeled as T0-T5) as a function of time.

FIG. 15 is a plot of internal temperature as a function of time.

FIG. 16 is a plot of percent heater power as a function of time.

FIG. 17 is a plot of battery voltage as a function of time.

FIG. 18 is a plot of external temperature as a function of time.

Figure 27:
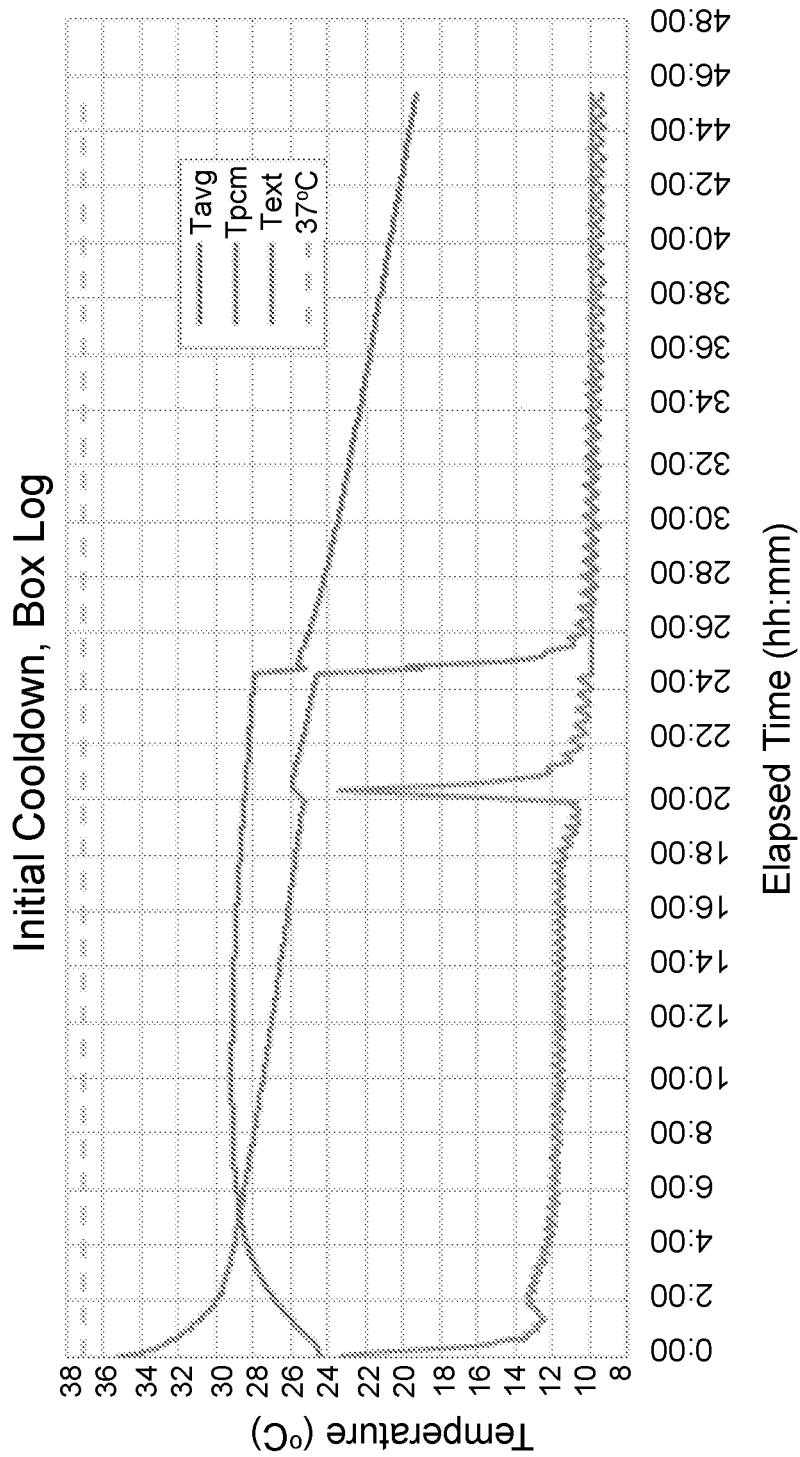

FIG. 27 is a temperature plot as a function of time for initial cool-down following box assembly. The phase change material (PCM) temperature (Tpcm) cools rapidly to 30° C. to about 25° C., then rapidly cools to 10° C. The payload temperature (Tavg=AVERAGE(T0 . . . T5)) begins cooling after a delay. This suggests the PCM releases significant latent heat between 30° C. and 24° C. when cooling.

Figure 28:
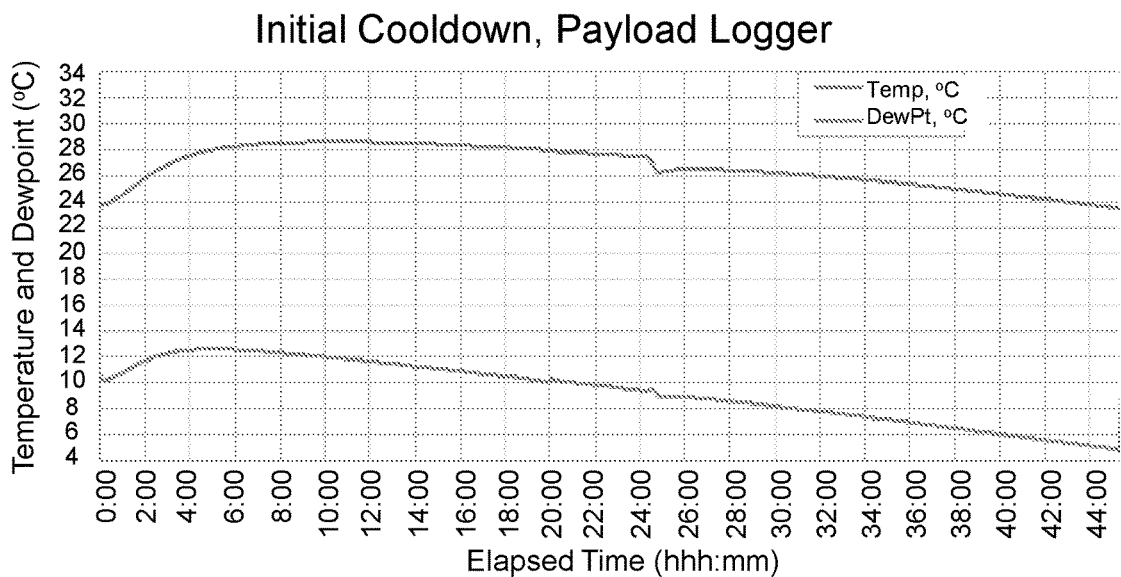

FIG. 28 is an independent payload logger that confirms Tavg of FIG. 27 is real.

Figure 29:
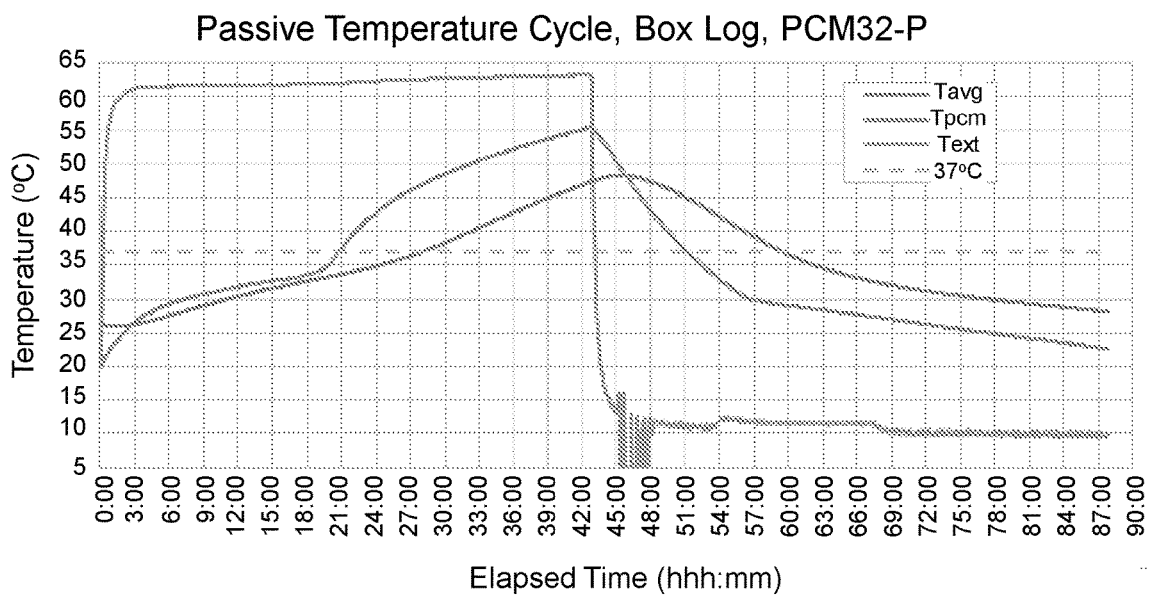

FIG. 29 is a box log of a passive temperature cycle. The PCM is effective at delaying warming of the payload to 37° C. for 27 Hrs. During cool down, the PCM also delays the payload cooling far below 37° C. The oscillation of Text at 45 Hr/12° C. is a recurring issue believed to be caused by condensation on the temperature sensor.

Figure 30:
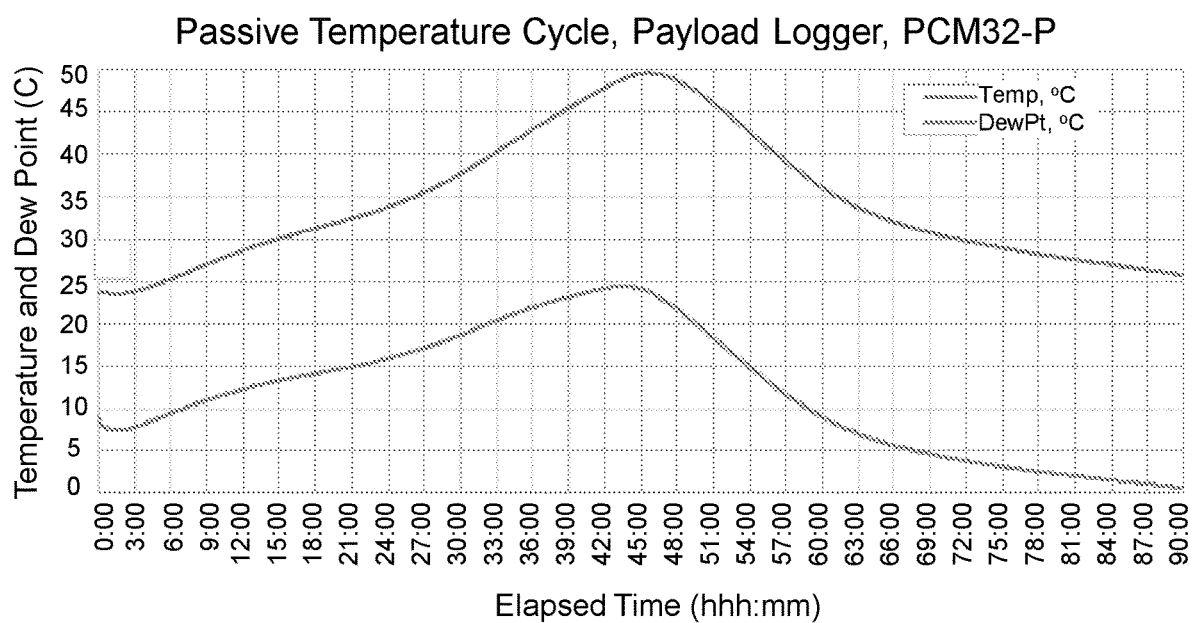

FIG. 30 is payload logger data, specifically temperature and dew point as a function of time.

Figure 31:
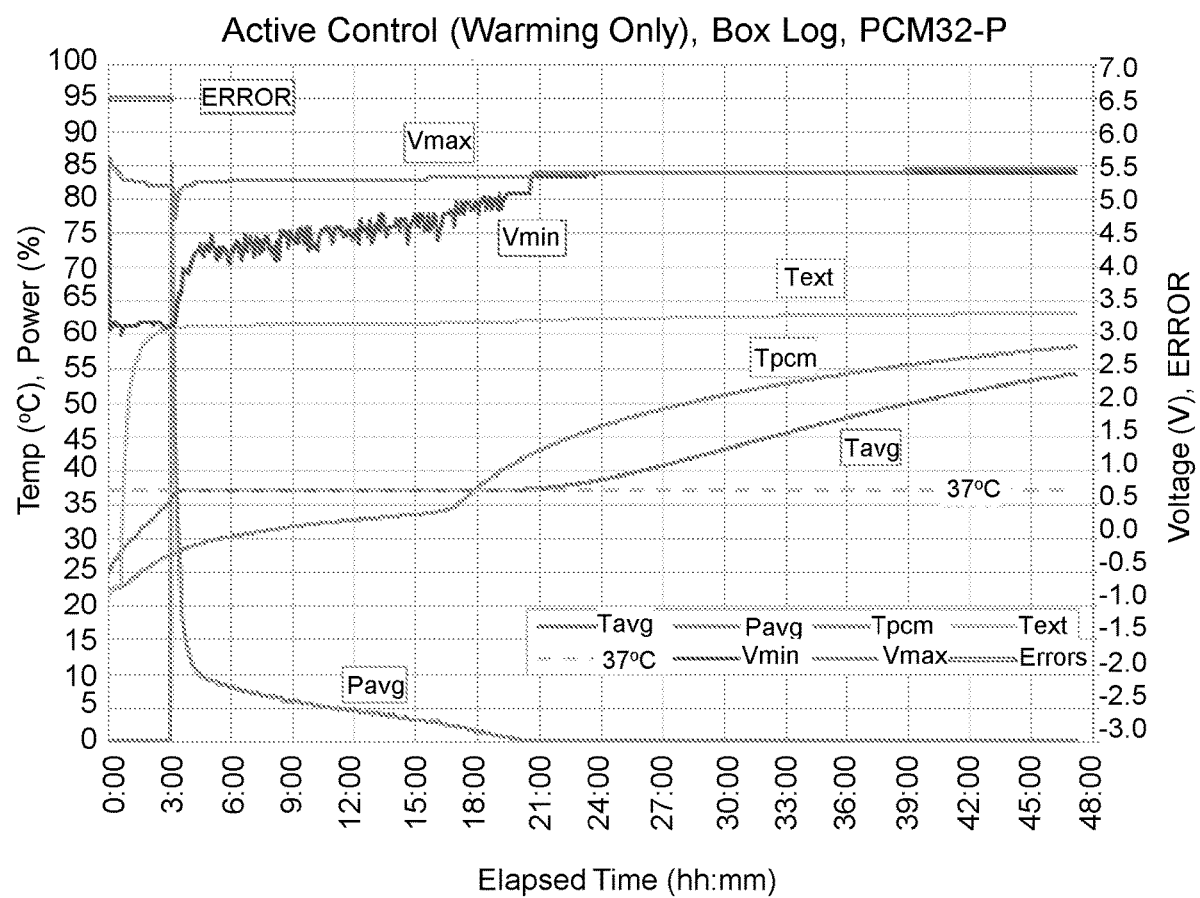

FIG. 31 is payload logger data for active control (warming only), including for temperatures (T), power (P) and voltage (V). Error conditions are also monitored. Vmax and Vmin and the Maximum and Minimum battery pack voltages measured for each 5 minute logging period.

Figure 32:
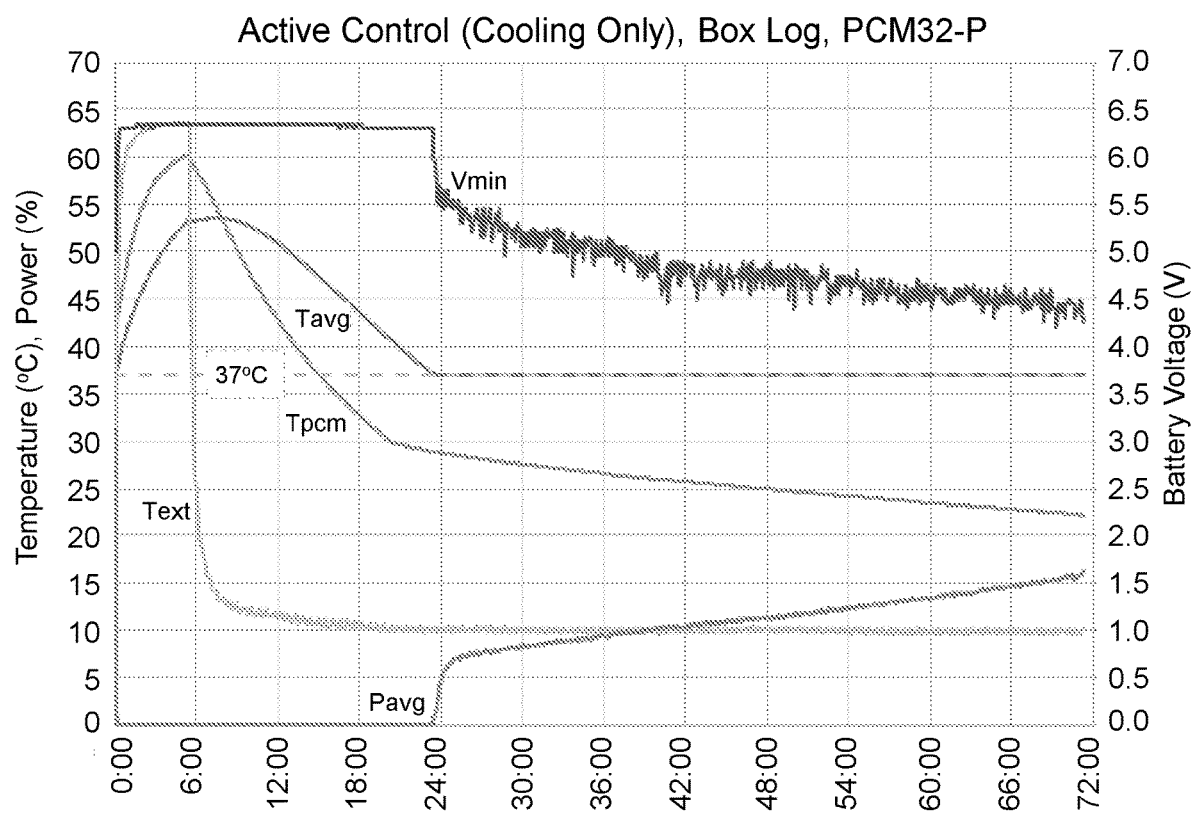

FIG. 32 is payload logger data for active control (cooling only). Box Log. The high contact resistance required some time to diagnose and address. The open box was placed back into the incubator to rewarm the PCM for the first 6 hours before being closed and moved to the refrigerator. At 20:50 (29.7° C.), the PCM began delaying cool-down. The test was terminated before the PCM heat was depleted.

Figure 33:
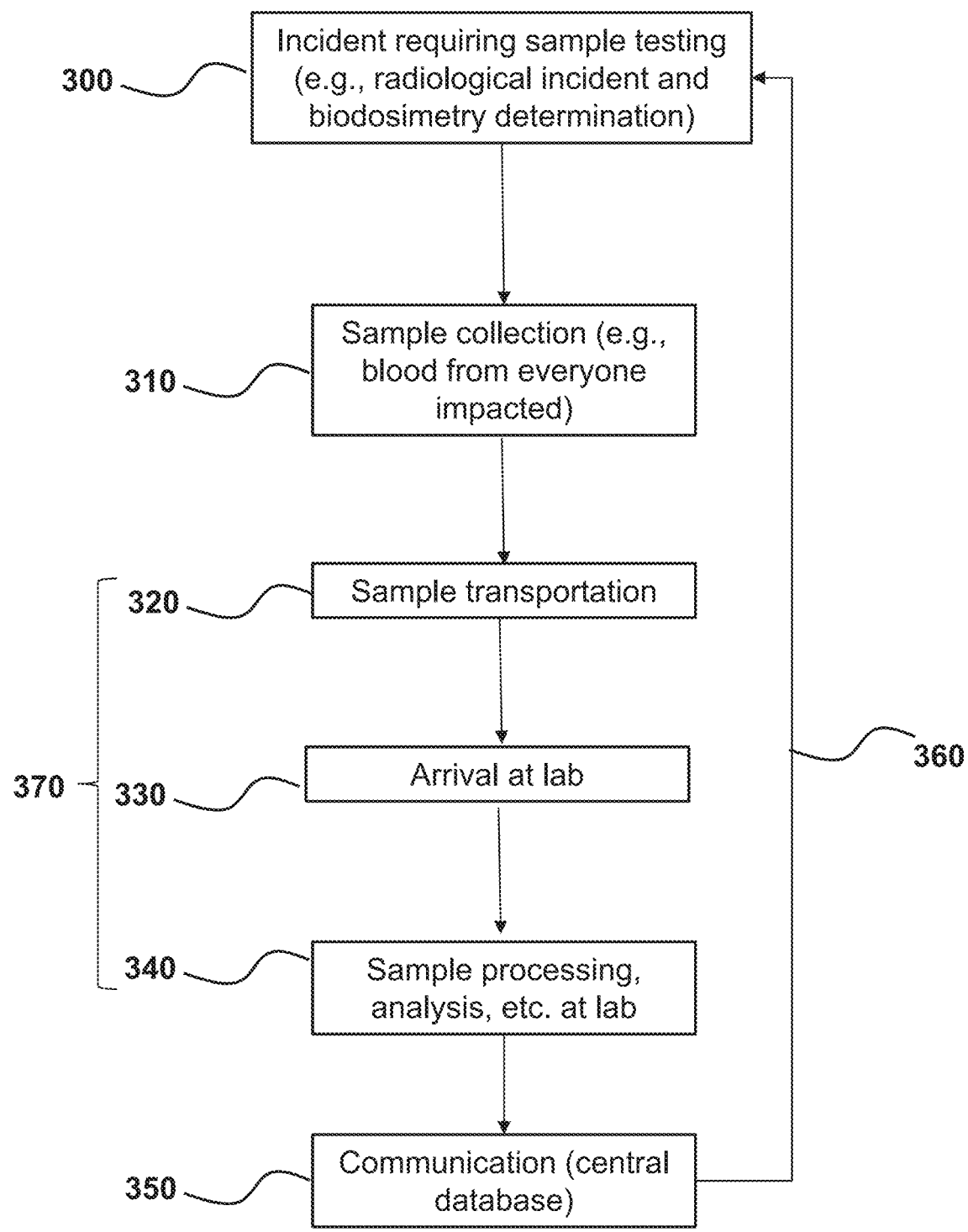

FIG. 33 Flow chart summary of a method for preprocessing a collected sample associated with a radiological incident.

Figure 34:
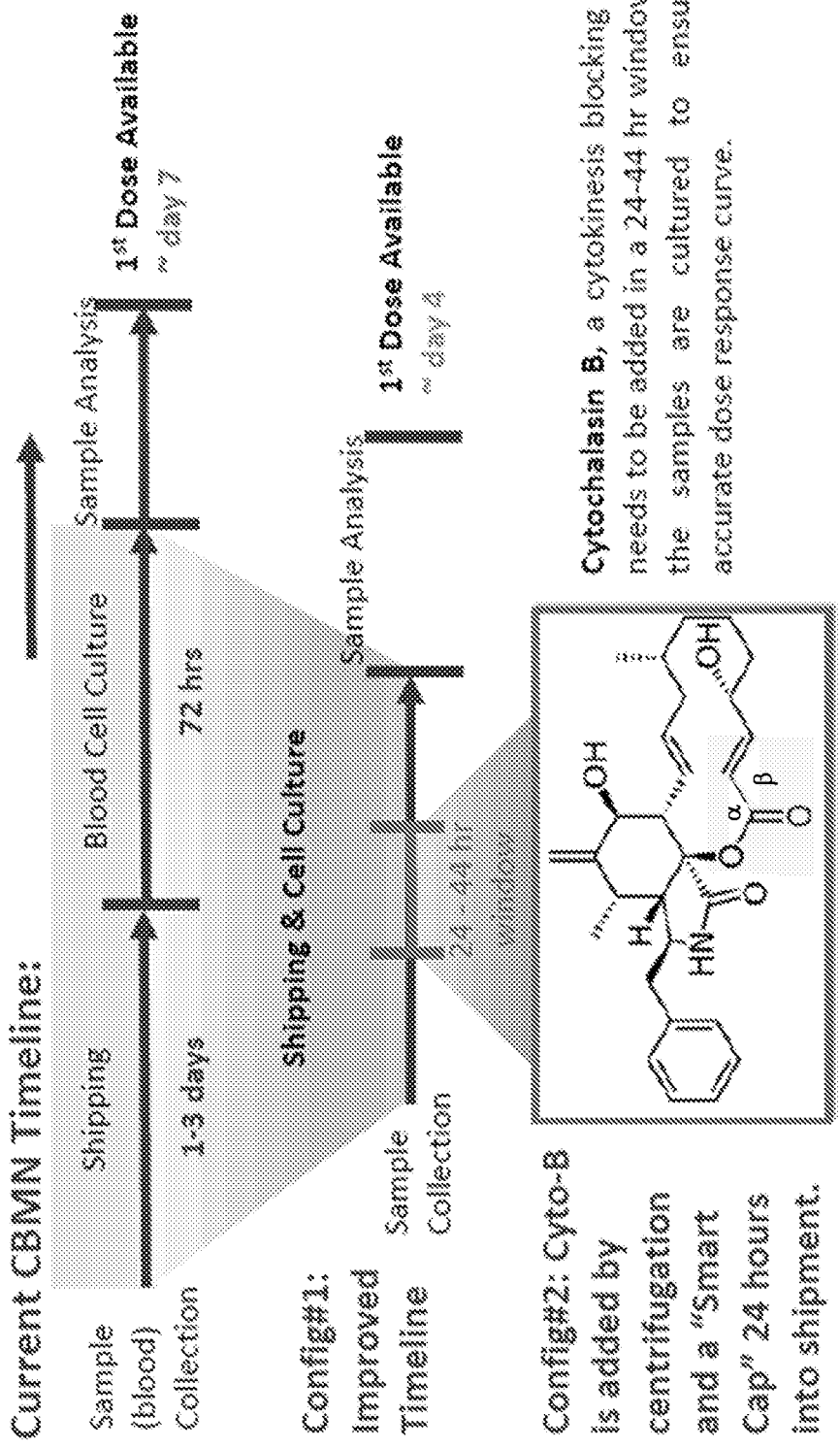

FIG. 34 is a time course illustration of the steps 320 330 340 of FIG. 33, reflecting an about 7 day time for obtaining useful information about radiological dose from the time of sample collection.

Figure 35A:
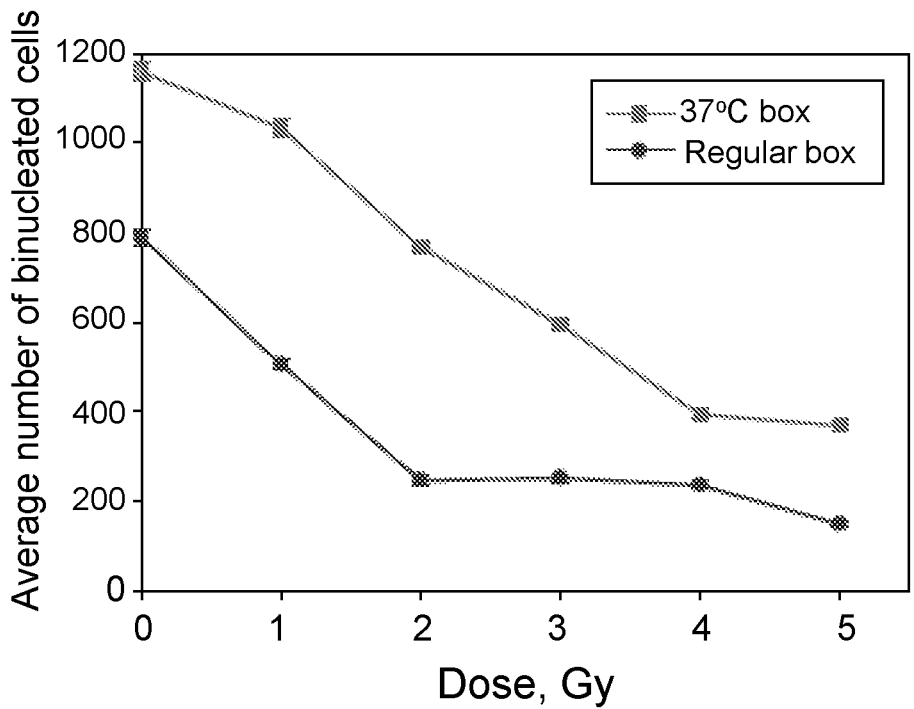
Figure 35B:
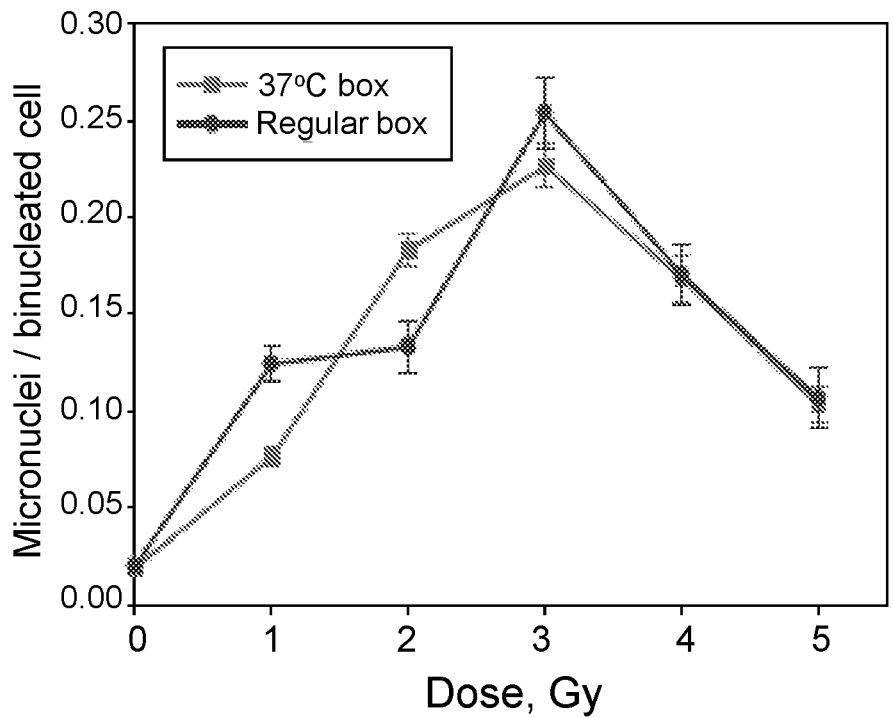

FIGS. 35A and 35B are dose-response curves for radiation intensity exposure and average number of bincucleated cells and ratio of micronuclei/binucleated cell, respectively, for each of 37° C. incubation and a regular container.

Figure 36:
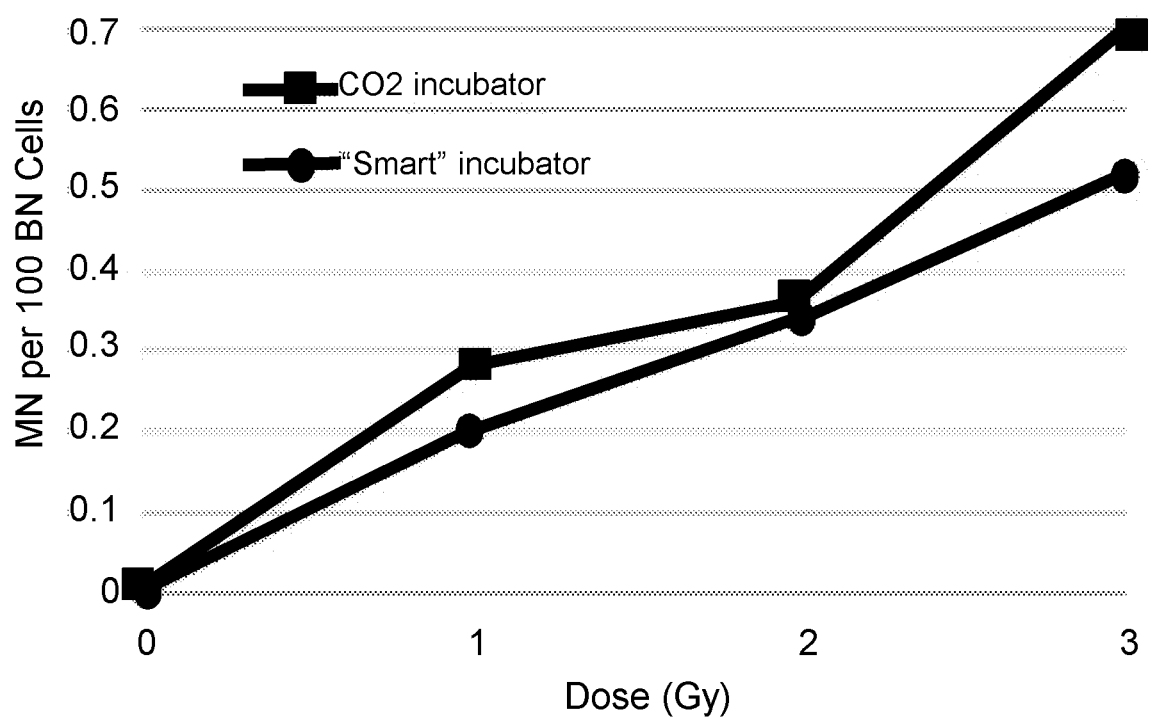

FIG. 36 is a dose response curve for radiation intensity exposure and micronucleated (MN) per 100 binucleated (BN) cells.

DETAILED DESCRIPTION

"Sample" is used broadly herein to refer to any material that can be collected at a first location and sent to a second location that may have specialized equipment and/or expertise in obtaining desired information related to or from the sample. The sample may be a biological sample, or contain biological constituents. Examples of samples include, but are not limited to, a bodily fluid (blood, saliva, urine, cerebrospinal fluid, etc.), a tissue sample or an environmental sample (water, soil, fume), a food sample. Of course, the methods and systems provided herein are compatible with any number or kind of samples, so long as they are capable of being shipped in a container and, it is desired to control and/or monitor one or more parameters associated with the storage and/or sample container that holds the sample. The sample may be stored within a sample container, with the sample container then stored within the storage container.

"Sample processing facility" refers to the location at which the biological sample is processed to provide desired information about the sample. In particular, the sample processing facility may be used to obtain information relevant for a diagnosis or a therapy. The methods and systems provided herein are useful for any of a range of facilities, depending on the application of interest and the associated biological sample.

"Preprocessing" refers to a processing of the sample during transit that would otherwise be required to occur at the sample processing facility. In this manner, the instant preprocessing results in a reduction of time required at the processing facility, thereby decreasing the time required to obtain desired information about the sample.

"Processing parameter" or "biological sample processing parameter" is used broadly herein to refer to activity required at the sample processing facility to obtain useful information from the sample that is being delivered to the facility. Accordingly, the processing parameter may be the amount of time required at the facility in order to obtain the desired information from the sample. Similarly, the processing parameter may refer to a particular step or the total number of steps to be performed at the facility. An improvement in the processing parameter may then refer to a decrease in the processing time, a reduction in the number of processing steps (or a decrease in time of one or more of the processing steps), or an improved integrity of the sample outcome, such as improved sensitivity, reliability and/or accuracy, compared to an equivalent sample that has not undergone the preprocessing steps during transport. An improved processing parameter may reflect that the number of steps required at the sample processing facility is decreased. This may be achieved, for example, by performing one or more of the steps during transit.

"Storage container parameter" refers to the ability to control a parameter in the storage container that, in turn, affects the sample that is stored in the container. For example, the parameter may be a parameter that directly affects biological material, such as an environmental control, including temperature and/or humidity. The parameter may also be a parameter that has a more indirect effect on the biological material, such as control of a device that is useful in processing of the sample, such as a switch, power, fluidic control (valve, pump, etc.) to provide for reagent introduction, fixative introduction, isolation, centrifugation, mixing, rinsing or washing, separation of a sample constituent, fluidic and/or gas manipulation.

"System parameter" refers to a variable that can impact the preprocessing. For example, an external environmental parameter such as an impact force or temperature is considered a system parameter.

"Operation parameter" refers to a variable that can impact the preprocessing and is generally associated with the system. Examples include power, including a main battery voltage, power disconnect event (that may, in turn, be tied to a system parameter such as an impact force), or component malfunction. More generally, an operation parameter is indicative of system status and is helpful for troubleshooting issues that could impact control of a storage container parameter.

The following examples further illustrate the invention but, of course, should not be construed as in any way limiting its scope.

Example 1: Temperature Characterization of a Smart Shipping Container

This example characterizes a smart shipping container.

Cold shipments are common, making use of water ice, gel packs, phase change mass, and dry ice to keep the shipment cool. Much less common are warm shipments. The only method of keeping a shipment warm is by using a phase change mass. Phase change mass offers poor temperature control, and is insufficient for incubation purposes.

Figure 1A:
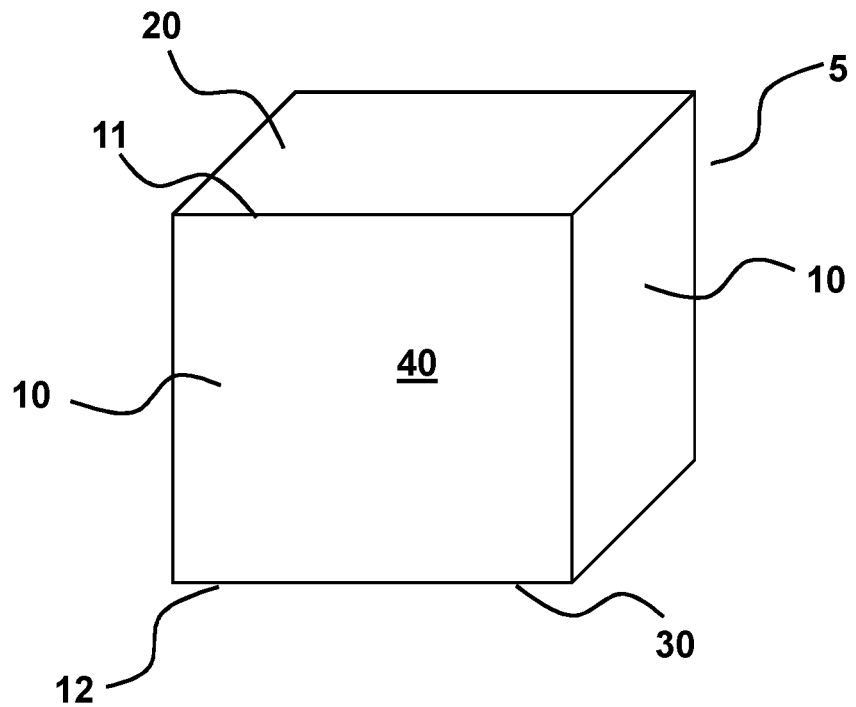
Figure 1B:
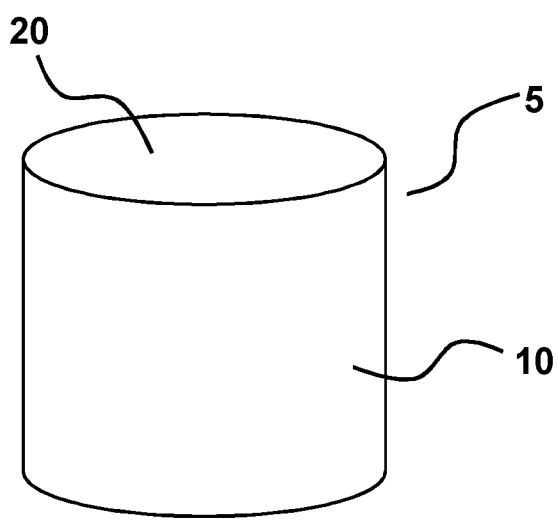
Figure 1C:
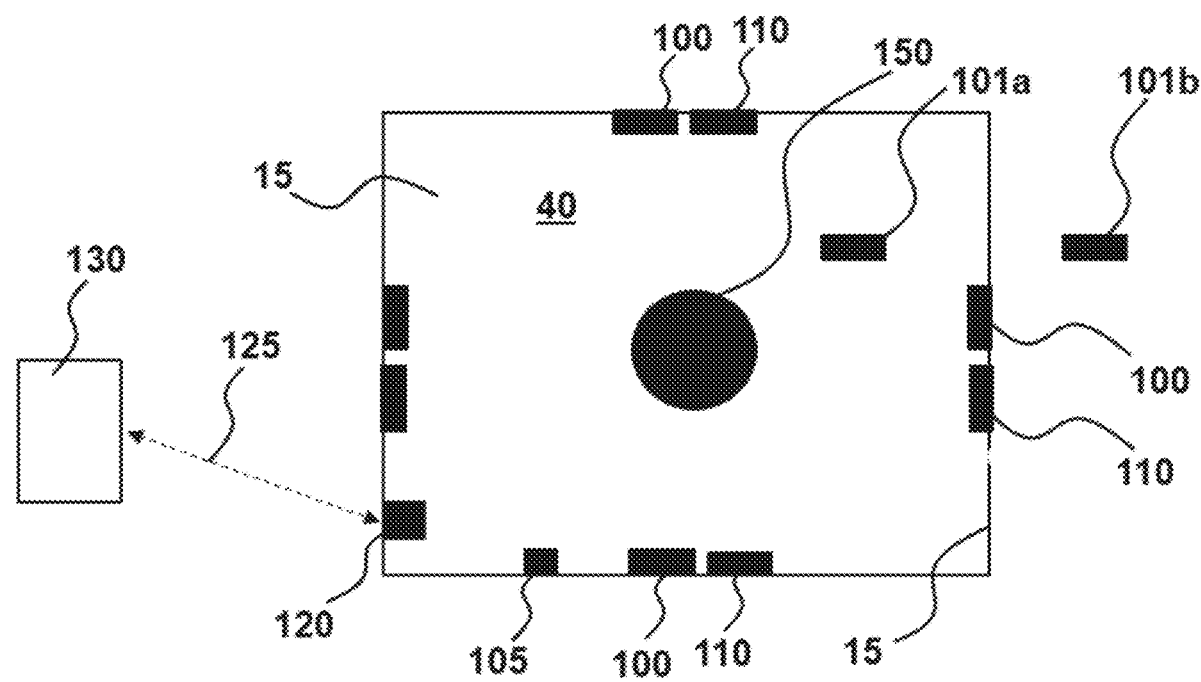
Figure 1D:
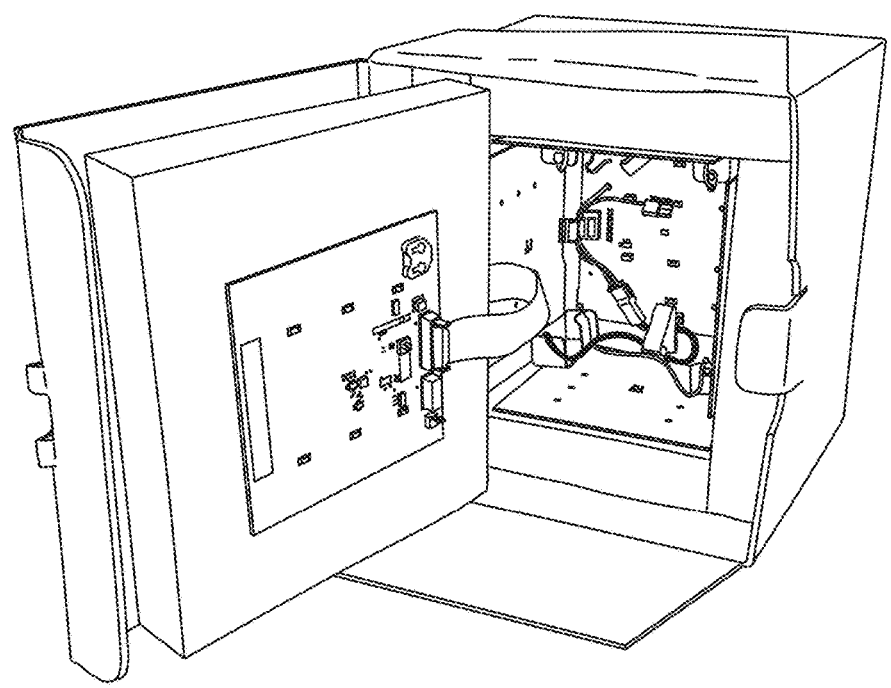

This example introduces a heated shipping box intended to function as an incubator while in transit (FIG. 1A-1E). FIG. 1D illustrates power for heating can be provided using common, off-the-shelf batteries. The system is enclosed inside a common Styrofoam insulated box. Temperature control is as good as most lab incubators, maintaining a programmed temperature of 37.0° C.±0.1° C. for the duration of the shipment. The box records system performance and significant events. Options for increased operating endurance and operation at other temperatures are available.

Figure 1E:
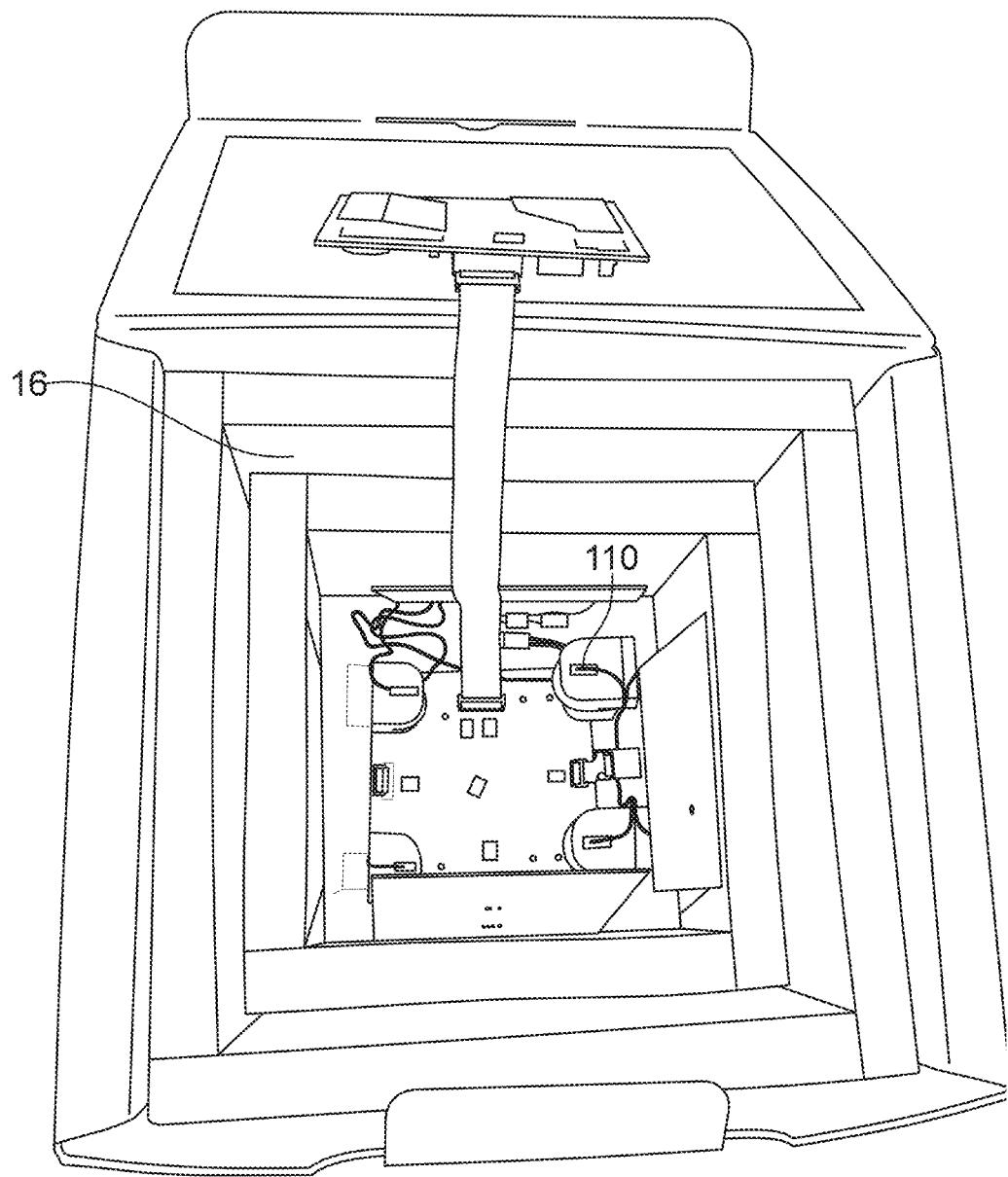

The storage container 5 may have multiple side walls 10 (FIG. 1A) or a single side wall 10 (FIG. 1B), with top 20 and bottom 30 walls to form a storage volume 40. FIG. 1A illustrates a 6-sided box with four interconnected side-walls, with each side wall having a top edge 11 and a bottom edge 12 that further define and form storage volume 40. Inner surfaces 15 (see, e.g., FIG. 1C) of the side, top and bottom walls also are described as forming storage volume 40. Temperature sensors 100 are connected to the inner surface(s) of side wall(s), top wall, and bottom wall. Depending on geometric configuration such as surface area of the walls, operating conditions, and desired temperature distribution sensitivity, more than one temperature sensor may be connected to the inner surfaces. Similarly, thermal actuators 110 may be connected to the side wall(s). Optionally, additional temperature sensor(s) 101a 101b may be used to measure temperature in the storage volume 40 and/or a temperature outside the storage container. A position (GPS) sensor 105 may be used to track the position of the storage container. A wireless transmitter and/or receiver 120 may be used to wirelessly transmit and/or receive data 125 with an external controller 130. A temperature-sensitive cargo 150 (including a biological sample stored in a biological sample container) may be positioned in the storage volume. The cargo may be secured to any of the side walls, including to the bottom wall inner surface 15. FIG. 1E illustrates a thermal actuator 110 and a PCM 16 layer formed as one layer of a multiple layer wall, with insulative layers adjacent to the PCM and a thermally-conductive innerfacing surface. Depending on the expected environmental conditions, a heat storage material can be selected. For example, a hot environment, such as Phoenix, Ariz., that may have an environmental temperature up to about 50° C., may have a PCM with a phase change at about 37° C. To prevent the storage volume from going over 37° C., a peak phase temperature slightly below 37° C. may be used, wherein the starting temperature in the storage volume is below 37° C.

Temperature control: An important goal is temperature control of the payload, maintained for at least 36 hours (long enough for overnight shipping). The payload was to be temperature controlled to 37.0° C. in any environment expected during shipping. As the first revision of this system implements heating only, external temperatures above 37° C. may be briefly endured.

Power Sources: The system uses 4 alkaline D cells to power the heaters and general system operation. If longer endurance is required, an option is to increase the number of D cells used in the main battery pack.

A 20 mm diameter coin cell (CR2032, or CR2016/20/25) powers the system, excepting heaters, whenever the main battery pack momentary disconnects due to impacts experienced during shipping.

Logging Data: To evaluate system performance, select parameters from system operation are periodically captured for read-out later. Data recorded include the date and time of the snapshot, all 7 temperature sensor readings (6 panel sensors and 1 tethered sensor), all heater power levels (6 panels), the main battery voltage (4 D cells), and any significant events that occurred since the last snapshot.

Time Keeping: Accurate data logging requires keeping track of time. A 32.768 kHz "watch crystal" is used as the accurate time base due to its low power requirements and frequency stability over temperature. This is the timing basis for the Real Time Clock (RTC), data logging, and communications.

Communications: Communications with a PC is required for initializing the RTC and downloading the internal data log, but also allows for configuration and calibration of system parameters, and for interactive operations (extracting raw sensor data while tuning the PID temperature control function).

Heating Each surface of the payload volume includes a temperature sensor and a heater. When heating is enabled, the temperature sensor is read to control heater power. Since each side of the box is controlled independently, conditions such as a cold wind blowing onto one side of the box results in extra heating only for that side.

System Layout: Four identical Printed Circuit Boards (PCBs, or panel), each implementing a temperature sensor (located at the center), a heater switch transistor, and heater resistors arranged around the board are attached to the four interior sides of the insulated box, and are connected to the bottom PCB (FIG. 1D).

The bottom board includes the circuits of a side PCB and connects all circuits between the 4 side boards and the master board. These circuits include: Sensor Communications; Heater Control; Main Battery Power: Regulated 3V Power.

The master (top) board includes the circuit of the side panel as well as: Accepts Main Battery Power; Provides Regulated 3V Power; Reads All Temperature Sensors; Controls All Heaters; Stores System Data In Non-Volatile Memory; Powers System From Coin Cell When Main Battery Disconnects; Provide Communications With PC; Stores Calibration Data; Operates Real Time Clock (RTC). Four shock resistant D cell holders are mounted to opposing side boards, and are connected to the bottom board using its own wiring harness.

Operation

Start-Up and Shipping: Four fresh D cells are installed into the box. The coin cell may also require replacement. When the system is turned on, heating begins immediately, and the time is initialized to 01/01 00:00. Data logging begins at that time. If necessary, the box can be loaded and shipped with no further action.

The time can be set using the TIME command when connected to a computer. Data logging then restarts from that time. Heating can be disabled using a STOP command—this begins a log download (the first few entries of the previous shipping session may be overwritten by the latest start-up). Heating and a new log are resumed using the START command.

The box is then loaded with its payload, and the tethered temperature sensor is placed as desired (outside the box is suggested, but internal to the payload is also possible). The box is then sealed and shipped.

When the box is received, the payload is removed and processed as required. Another PC can disable heating using STOP—this also begins the log download. If the log was not captured, it can be downloaded again with another STOP command.

Reception and the Data Log: System performance can be evaluated at the end of shipment by downloading the data log generated during shipping. Every 5 minutes, a snapshot of the system state is recorded. For each snapshot, for following are recorded:

Date (12/31) and Time (23:59) of the snapshot. Years are not recorded. Days for each month are correctly processed. Leap Days are not processed (February is always 28 days long).

Six panel temperatures (T0 . . . T5)—The temperatures (° C.) of each panel are recorded.

One tethered temperature sensor (T6)—this is a temperature sensor (° C.) on a short cable that can be embedded within the payload, or placed outside the box to measure the external temperature. Information/logging only.

Heater power (P0 . . . P5)—this is a better measure of the system activity than the temperatures, as the temperatures are being strictly controlled. T0 controls P0. The range is 0 (0%) to 255 (99.6%). To get the Percent Full Power, divide the Duty Cycle by 256.

Main battery voltage (VMIN, VAVG, VMAX)—As the main battery pack (4 D cells) discharges, its voltage decreases. When VMAX falls to 3.0V, the battery is considered depleted, and heating is disabled.

Various events—momentary battery disconnects due to impact, heating disabled due to depleted main battery, and internal errors.

During normal operation, various events or conditions occur, causing status flags to be set. At the end of each 5 minute period, these flags are recorded and cleared, thus recording their approximate times.

Flags exist for the following events: Heating Disabled; Main Battery Disconnect; Internal Power Too Low (Coin Cell); Various Resets.

The data log is a human readable text file, and may be imported to Excel or Matlab for processing.

Testing: Initial firmware development occurred using an externally powered system mounted in the Styrofoam box. A rough temperature calibration was performed using a high resolution temperature logger.

An alternative to adding batteries to increasing endurance is to use better insulation. If a longer operating endurance is required, and the number of batteries needed cannot be increased, replacing the Styrofoam box with a box formed from vacuum insulated panels remains an option.

Insulation: Initial development and testing used a Styrofoam box with similar shape and size as the Credo Vacuum Insulated Panel (VIP) box. The last test prior to moving the circuit boards to the VIP box was an endurance test. A fresh set of cells were installed to the box, then the box placed in a refrigerator at about 6° C. This set of cells operated the box for 10.1 hours.

The circuit boards were then moved to the VIP box. Fresh cells from the same lot were install, and the experiment repeated. This configuration operated for 57.9 hours, about 5.7 times longer than the same system in the Styrofoam box.

Office to Refrigerator (VIP): The Vacuum Insulated Panel box was placed into a refrigerator at about 6° C., and left for a 3-day weekend. The batteries were able to sustain the internal temperature for almost 57 hours. Heating was disabled when the main battery was fully discharged.

Figure 2:
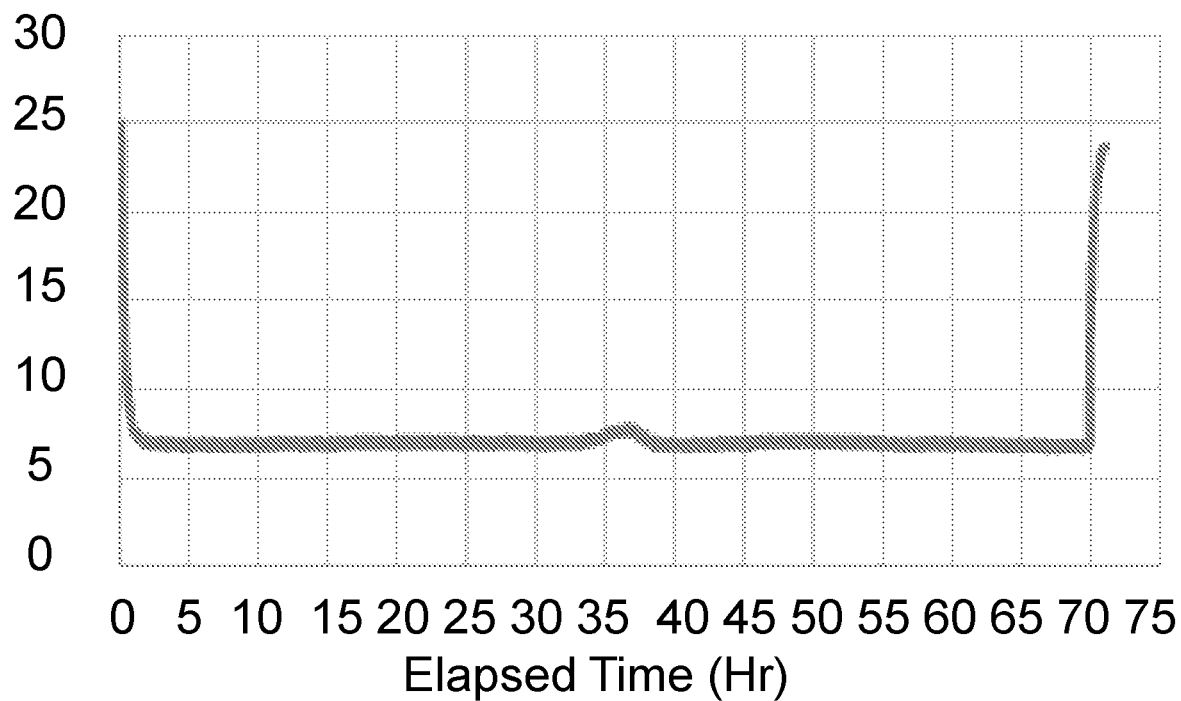
Figure 4:
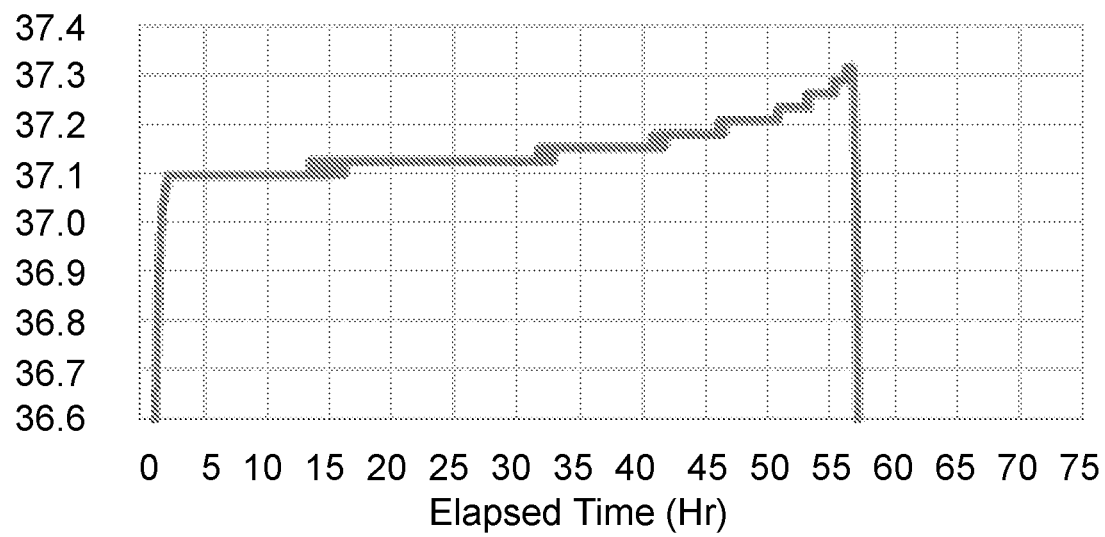
FIG. 4 is a plot of payload temperature as a function of time.

Time course plots are obtained for the external temperature (FIG. 2) and internal temperature (FIG. 4) as reported by independent temperature loggers (HOBO Pro V2 Temp/

Figure 3:
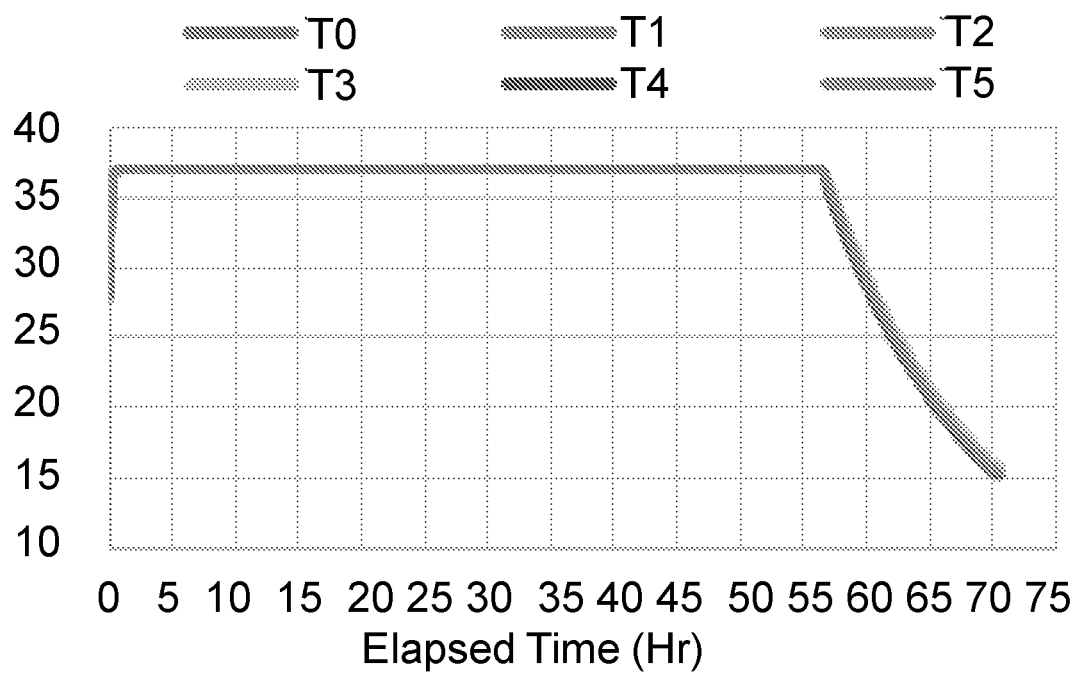
Figure 5:
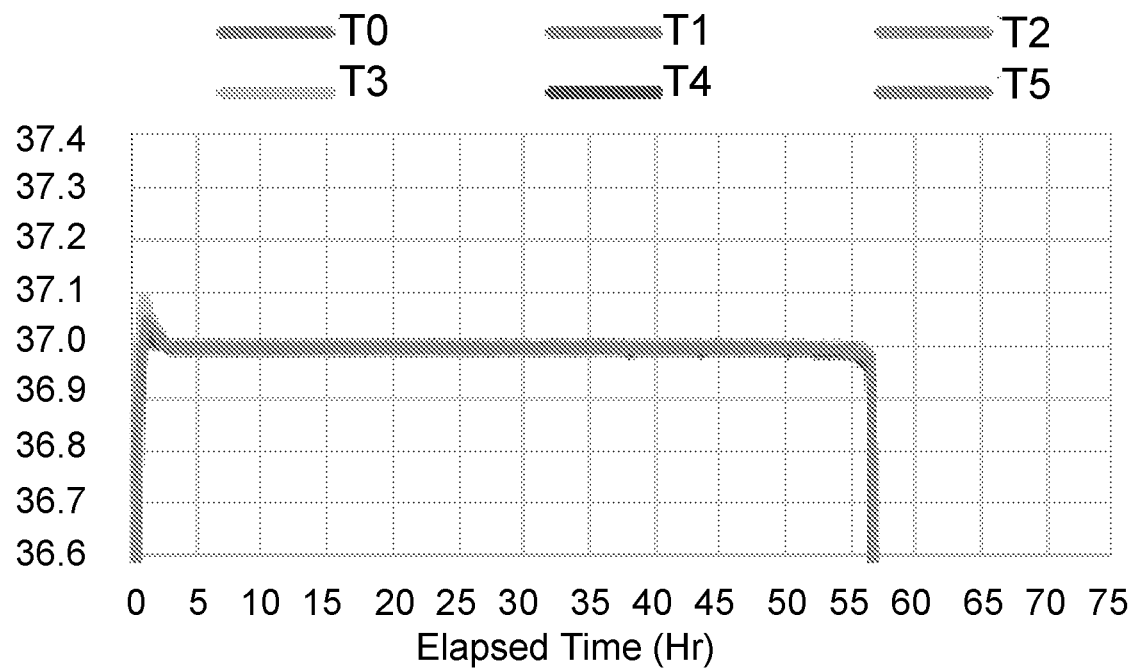
FIG. 5 is a plot of panel temperature as a function of time.
Figure 6:
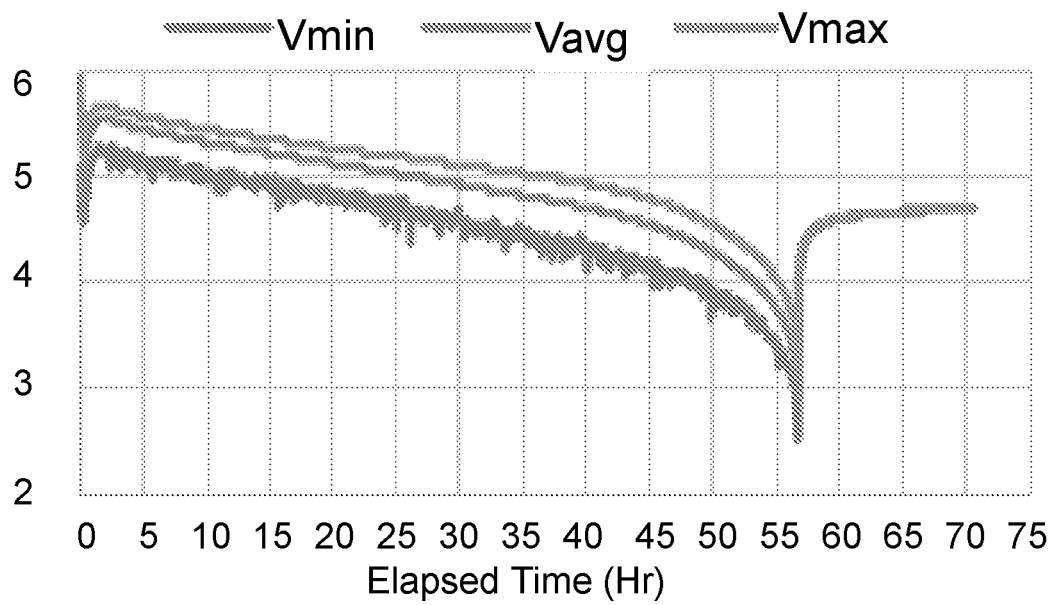
FIG. 6 is a plot of main battery voltage as a function of time, with minimum, maximum and average voltages.
Figure 7:
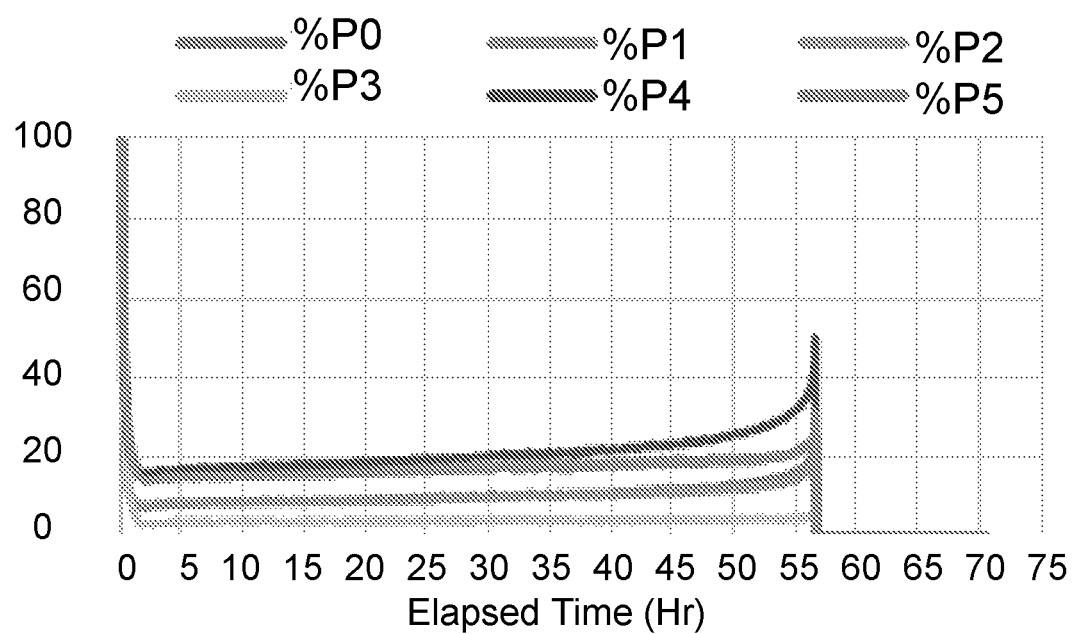
FIG. 7 is a plot of panel percent max heater power as a function of time.

RH). Data from the internal log contains panel temperatures (FIG. 3 and FIG. 5), battery voltages (FIG. 6), and, panel heater power (FIG. 7).

The internal temperature rises as the batteries themselves generate more heat as they become depleted. Heater Power increases as the battery voltage falls to maintain constant average power.

Figure 8:
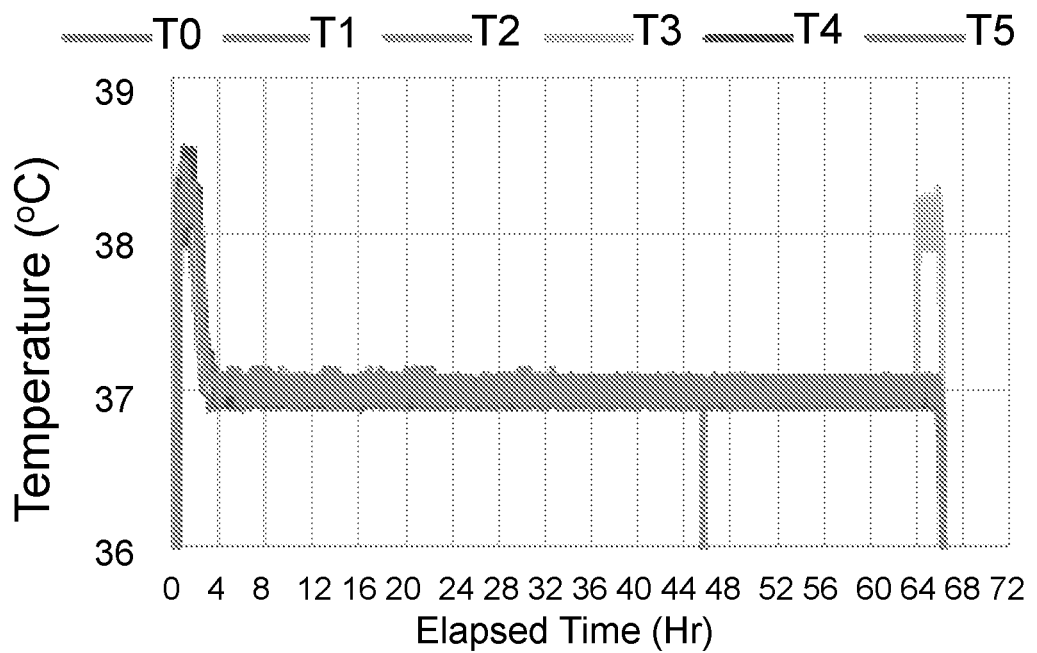
FIG. 8 is a plot of internal temperature as a function of time.
Figure 9:
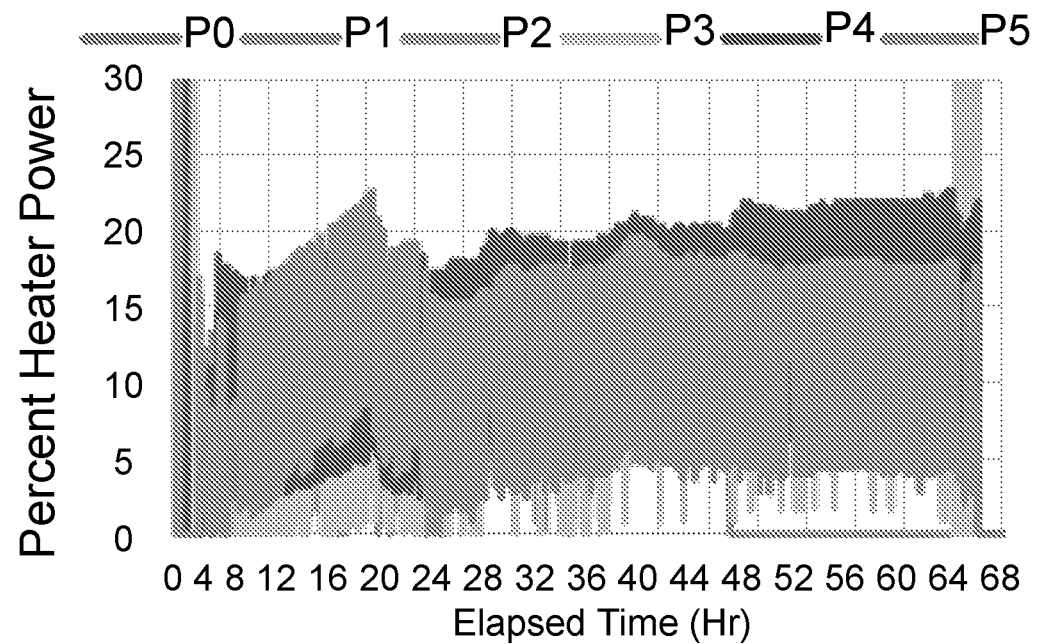
FIG. 9 is a plot of percent power as a function of time.
Figure 10:
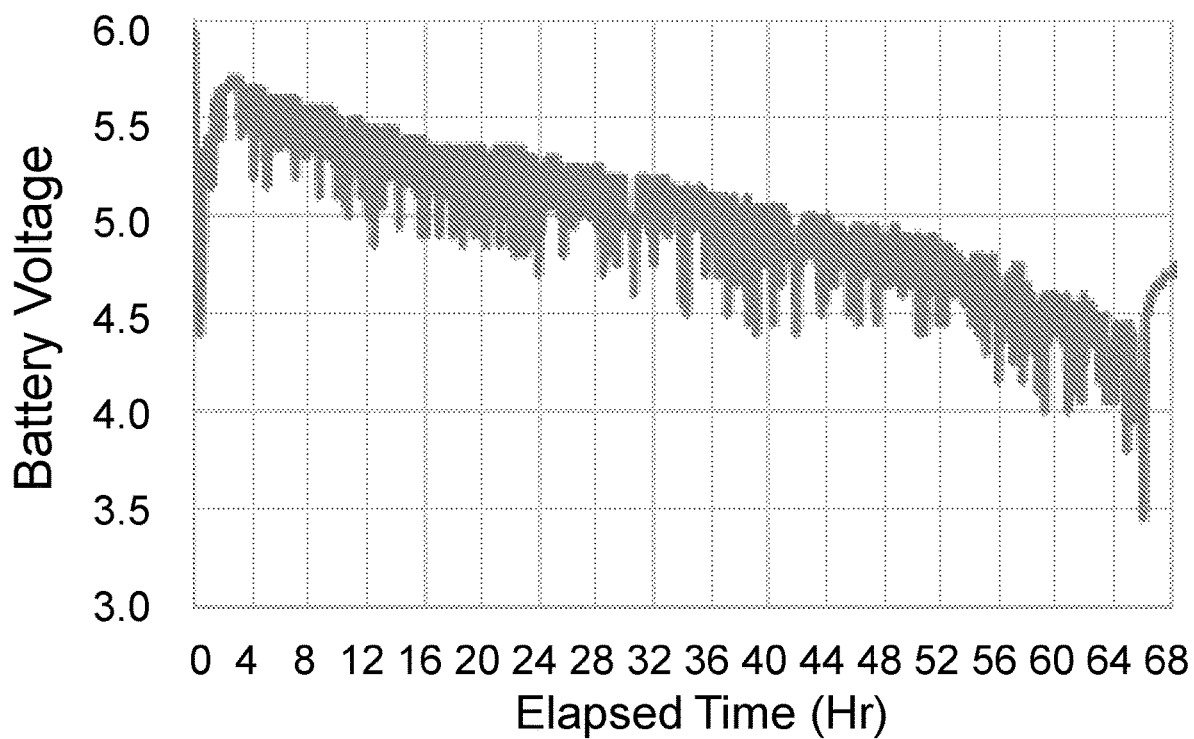
FIG. 10 is a plot of battery voltage as a function of time.

Shipping test (Winter): The heated box system was shipped from Phoenix, Ariz. (8.9° C. to 19.4° C.) to Long Island, N.Y. (1.1° C. to 8.3° C.). Four issues were discovered:

1. There was a large temperature overshoot to 38.5° C. due to a firmware error (FIG. 8).
2. The temperature sensor on Panel 1 (T1, side panel) failed at 45 hours (FIG. 8). The temperature indicated was 0.1° C., a signal indicating a loss of a temperature sensor. The heater power for that panel (P1) was disabled as a result (FIG. 9, expected response). Overall, the performance of the box was not impacted, showing robustness when responding to faults.
3. Heating was unexpectedly terminated early due to a low battery voltage at 66 Hours (FIG. 10). This was resolved by implementing Min/Max voltage measurements across each 5 minute record period. Heating is terminated when VMaxBat decreases to between 1.0V and 3.0V. (Less than 1.0V indicates a battery disconnect which requires a different response.)
4. At 64 Hours, T3 (bottom panel) measures 38° C. (FIG. 8), and is still applying full heater power (FIG. 9). There is no indication of a temperature rise anywhere else in the system. This appears to be a fault in the PID function, as heater power was toggling between 0% and 99.6%.

Shipping (summer): the heated box system was shipped from Phoenix, Ariz. (26.7° C. to 40.9° C.) to Long Island, N.Y. (17.8° C. to 21.7° C.) and back.

Figure 11:
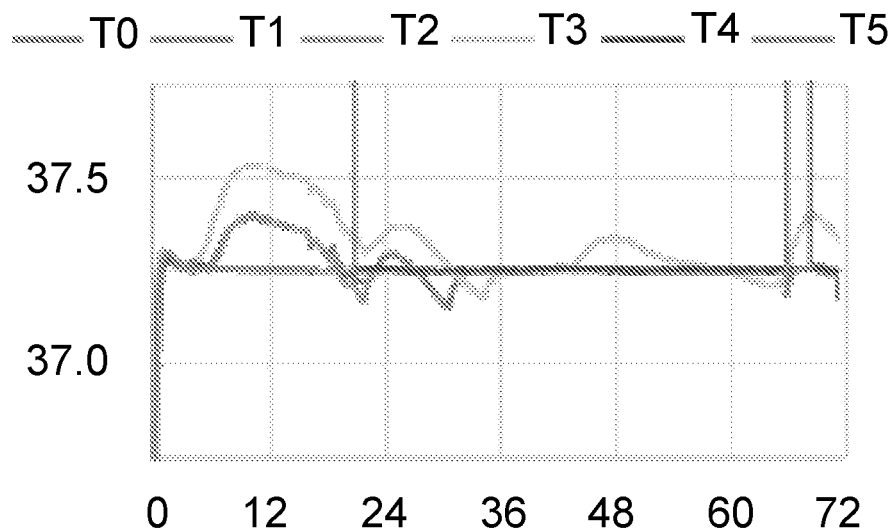
FIG. 11 is a plot of internal temperature as a function of time.
Figure 12:
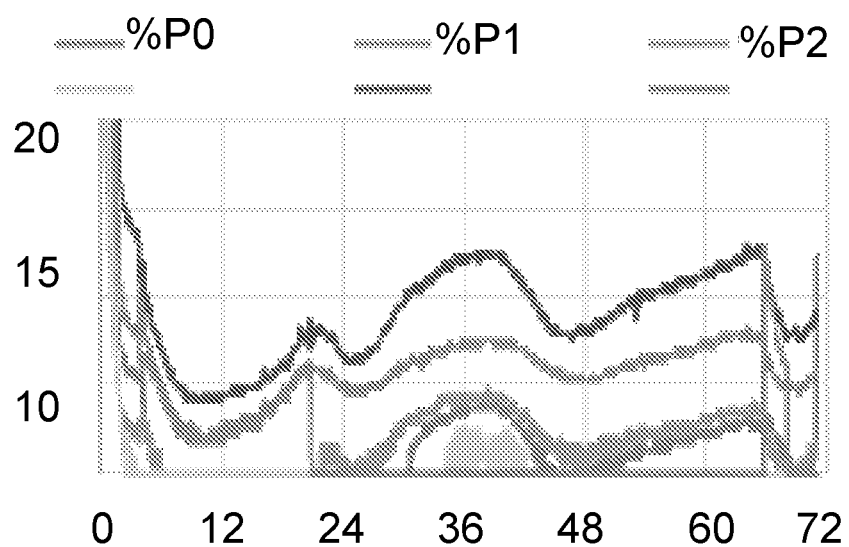
FIG. 12 is a plot of percent heater power as a function of time.
Figure 13:
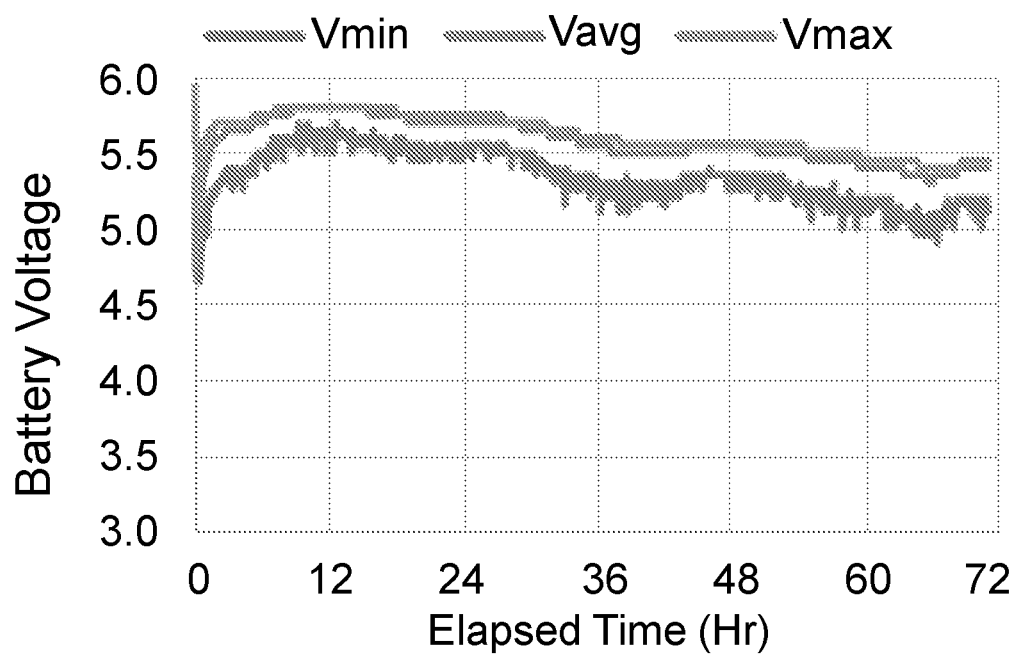
FIG. 13 is a plot of battery voltage as a function of time.
Figure 14:
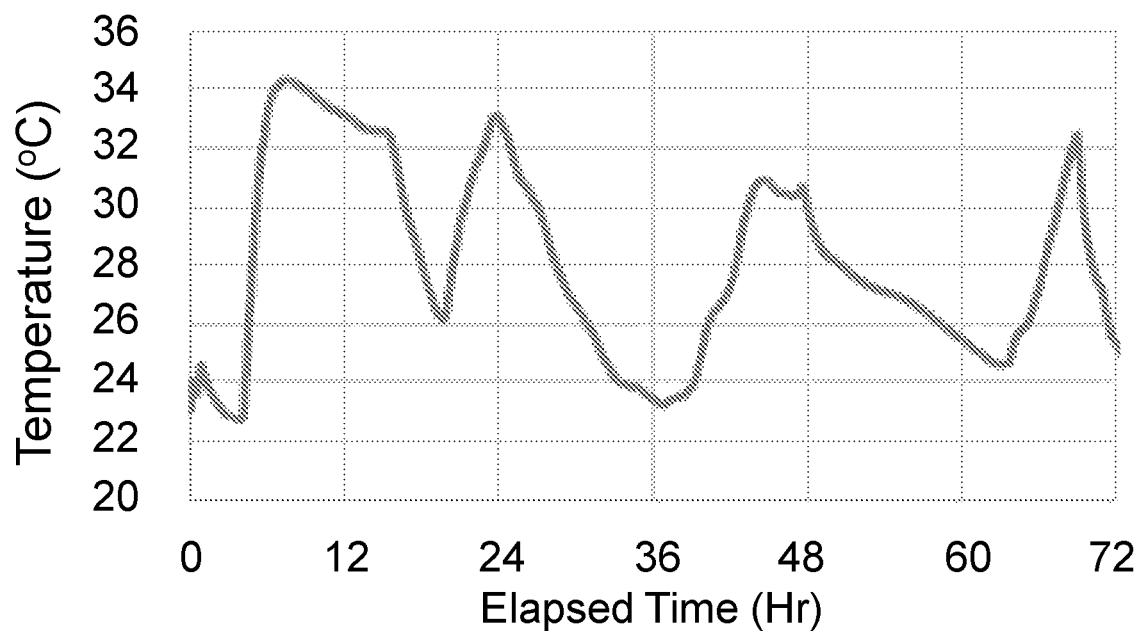
FIG. 14 is a plot of external temperature as a function of time.
Figure 19:
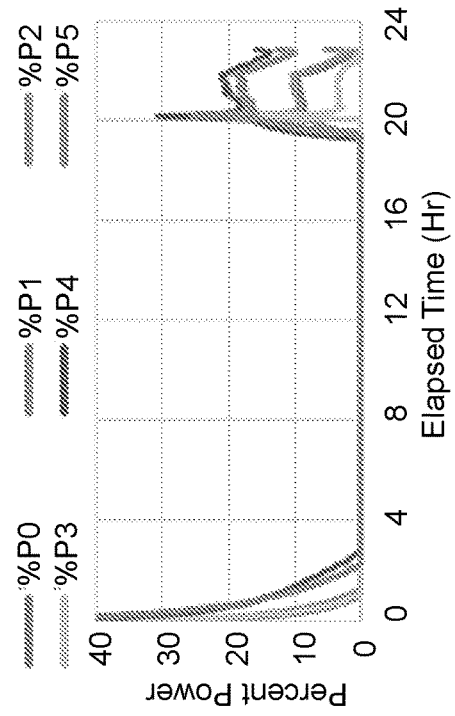
FIG. 19 is a plot of internal and external temperature as a function of time, wherein the shipping container is moved from room, to incubator, to refrigerator, with corresponding temperatures of 22° C., 47° C. and 6° C., respectively.
Figure 21:
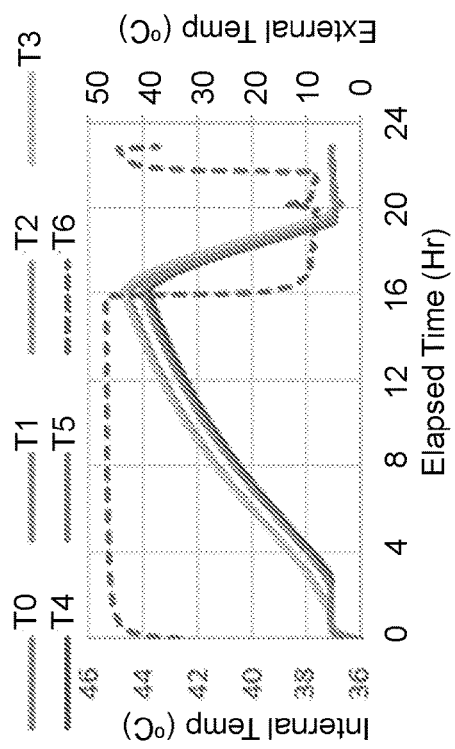
FIG. 21 is a plot of heater power (expressed as a percent) as a function of time for container movement from 47° C. to 6° C. to 22° C.
Figure 20:
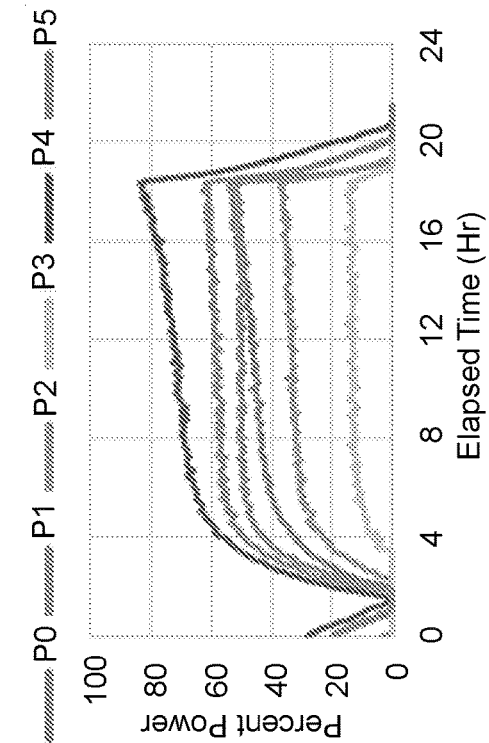
FIG. 20 is a plot of heater power (expressed as a percent) as a function of time for container movement from 22° C. to 47° C. to 6° C.
Figure 22:
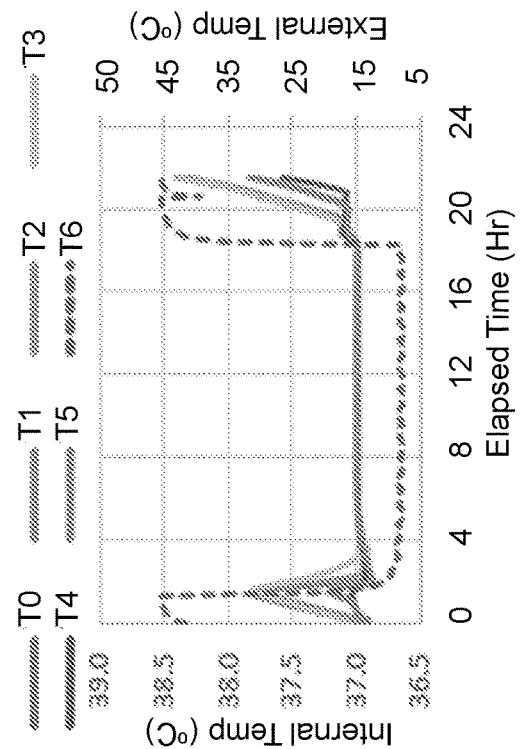
FIG. 22 is a plot of heater power (expressed as a percent) as a function of time for container movement from 47° C. to 6° C. to 47° C.

The start-up transient was limited to 37.1° C.; Temperature sensor T5 (side panel) is intermittent (FIG. 11); Heater P5 was disabled during T5 faults (FIG. 12, correct response); Various temperature sensors indicate uncontrolled temperatures above 37.2° C. (FIG. 11). These coincide with times where corresponding heaters are disabled (FIG. 12), and when the external logger indicates temperatures approaching 34° C. (FIG. 14). Conclusion: The box sides are too warm to control. (T0 top; T3 bottom; others are sides).

Long Island to Phoenix: Start-up transient well controlled (FIG. 15); Temperature T3 (bottom) is generally reading high temperature (FIG. 15). Heater P5 is disabled (FIG. 16) during those times. Other panels indicate high temperatures and disabled heaters when the external logger indicates external temperatures exceed 30° C. (FIG. 18); One battery disconnect event was captured at about 92 hours (FIG. 17) when the voltage fell below 3V. To detect disconnects that may occur more often and risk not being captured, additional methods are used.

Too Hot Outside? (Incubator at 47° C.): The summertime shipping revealed that the external temperature may rise high enough to become a problem when viewed from the perspective of a heat-only box. Testing in even higher temperatures was suggested.

The system may include a tethered temperature sensor (T6) placed inside the payload, or on the box exterior. Prior testing made use of independent temperature loggers as a stop-gap measure. If desired, one tethered temperature sensor may be placed inside the payload, and another tethered temperature sensor may be placed on the box exterior.

With T6 working, testing was performed by shuttling the box between a 6° C. refrigerator and an incubator set to 47° C.

Shipping (VIP): The heated box system is shipped from Phoenix, Ariz. (22° C. to 32° C.) to Long Island, N.Y. (12° C. to 22° C.) carrying blood samples.

The box had been preheated prior to loading with samples. Logging was started as the box was being packed. Temperature sensor T6 (external temperature sensor) was attached to the exterior of the top panel, within the external shipping box. In this location, it was able to measure the outside temperature while still being protected during shipping.

Two tilt detectors (TiltWatch® XTR; www.spotsee.io/tilt) were mounted on two adjacent exterior surfaces of the box (right angle surfaces). These activate at 80° tilt (on their sides). Both had tripped during shipment. The box was shipped via FedEx Priority Overnight, marked as containing Exempt Human Specimens. It was picked up at 13:28 and delivered the next day at 10:44 (15 hours later, all times NY).

Figure 23:
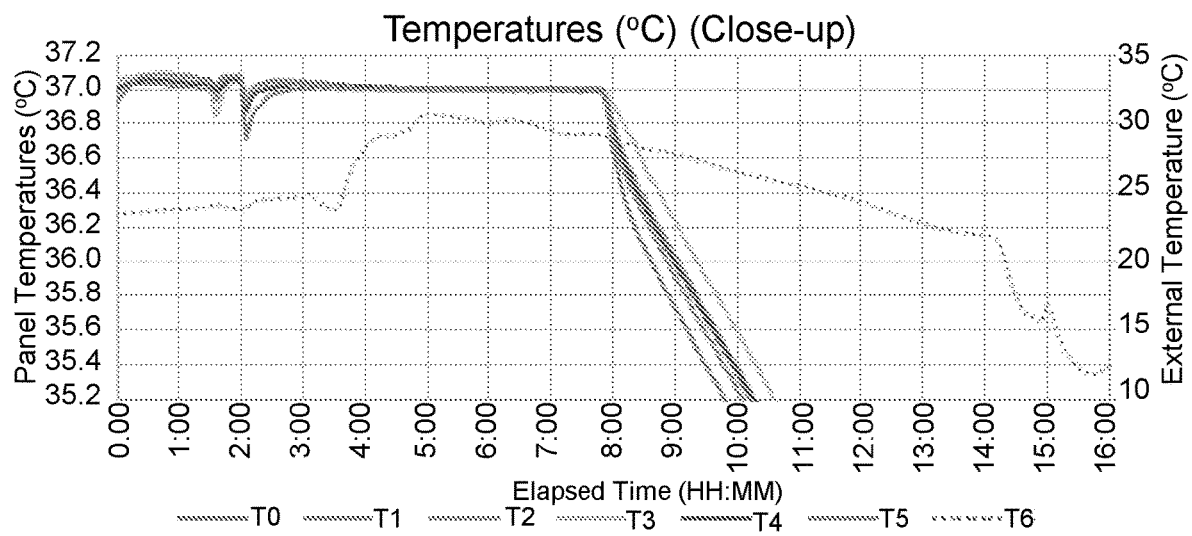
FIG. 23 is a plot illustrating temperature control for the first 16 hours for each of the six panels along with external temperature as measured by sensor T6.
Figure 24:
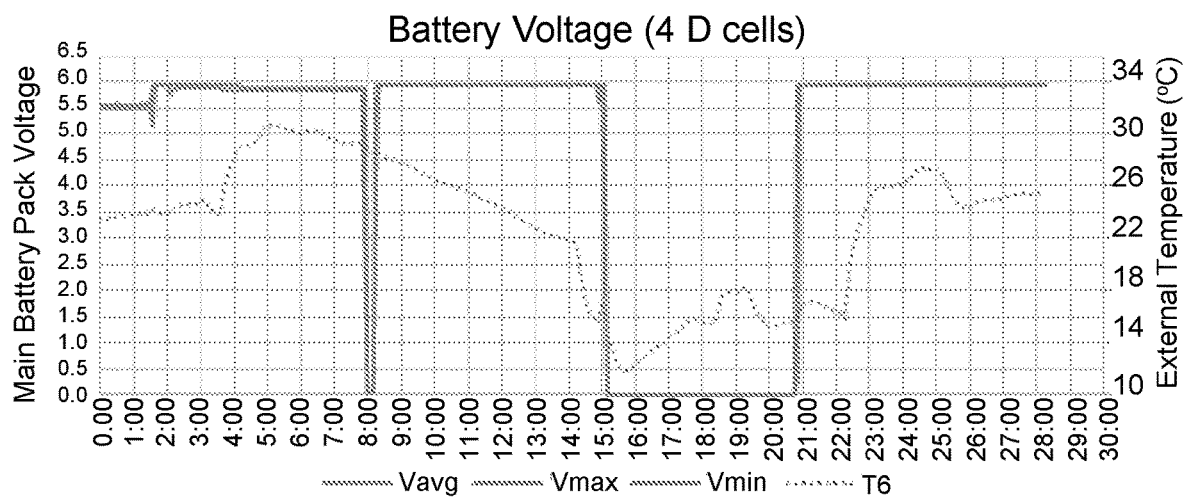
FIG. 24 is a plot of main battery pack voltage and external temperature as a function of time. The batteries are disconnected for about 20-25 minutes at 8 hours, with the shipment unpacked at 15 hours with the main batteries removed.
Figure 25:
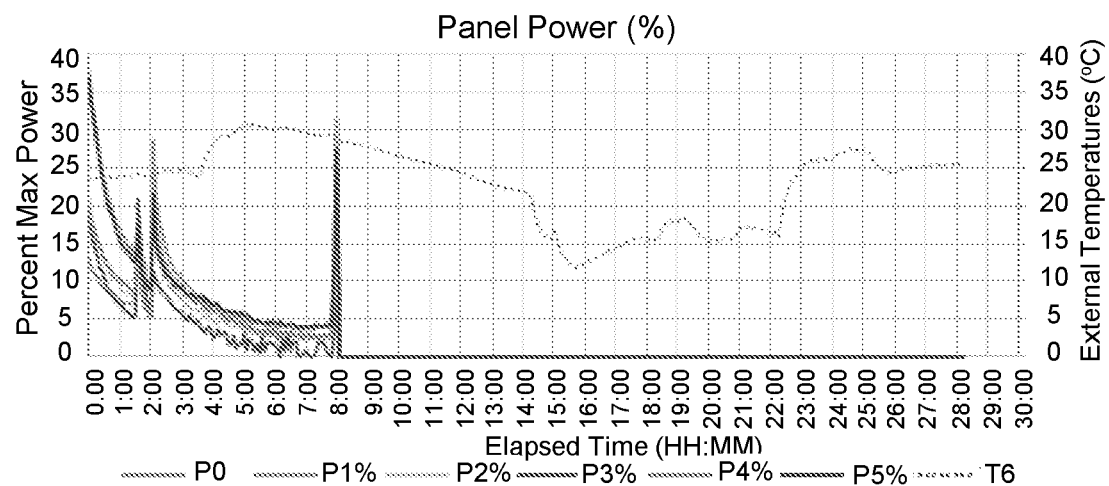
FIG. 25 is a plot of percent max power and external temperature as a function of time. Heater power spiked, presumably due to the box being opened, which caused disabling of heating.

Very good temperature control was maintained until 17:51 (Phx), or 8 hours after packing the box (FIG. 23). At that time, the batteries had been disconnected for 20-25 minutes. Panel heater power spiked at the same time (FIG. 25), suggesting the box had been opened, and the batteries removed and replaced. After that time, heating was disabled due to low main battery pack voltage.

Figure 26:
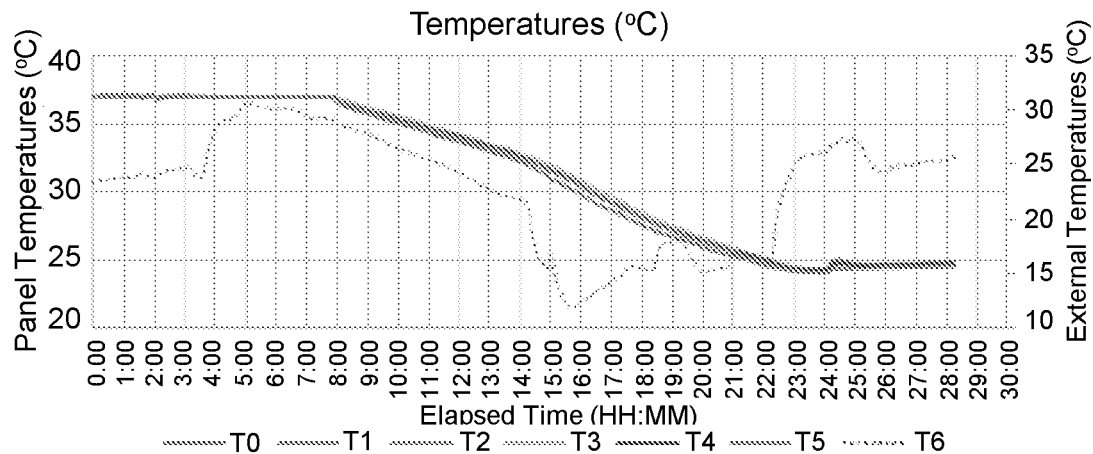
FIG. 26 is a plot of panel and external temperature as a function of time. The shipment was unpacked at about 15 hours.

Since heating was disabled, the box temperature began to fall (FIG. 26) until it was unpacked at 15 hours, temperature about 31.4° C.

Endurance: Two options are available to increase the system endurance:

Add additional D cells to the main battery pack. To double the endurance, use an 8 cell pack. Cells are connected in series, providing 6.0V, 7.5V, 9.0V, 10.5V, or 12.0V. As heaters are operating at a constant average power, their Duty Cycle (% power) are automatically reduced as needed. The battery voltage sense circuit would need modification and recalibration.

Change from the Styrofoam insulated box to a Vacuum Insulated Panel (VIP) box. Much of our work used a Credo 2 Liter box. Endurance will increase by a factor of 5 (i.e. from 20 fours to 100 hours).

Payload Volume: If a larger payload is required, the energy demanded by the heaters is proportional to the surface area of the box. Endurance is proportional to the number of D cells.

Replace the Tethered Sensor: The tethered temperature sensor could be replaced with a variety of other devices: A GPS receiver for determining time and location. This data can be logged. A cellular modem, making live data communication with the system possible at any time. Rough location services may be possible with help from the cellular carrier.

Communications with the payload for logging. For example, WiFi adaptor for use within the shipper's network (range of 100 meters). Bluetooth for command and status when in the presence of the box (range of 5 to 10 meters).

Example 2: Phase Change Material Characterization

Phase Change Material (PCM): The box currently includes PCM32-P PCM (see, e.g., Microtek Laboratories PCM Blend PCM32-P available at www.microteklabs.com/pcmblend). Various vendors specify the temperature characteristics differently, but all with a single temperature. Each of these materials must be evaluated to understand how they perform.

Dual Wall Box: The insulated box comprises a pair of boxes constructed using Vacuum Insulated Panels (VIP) (Pelican Biothermal Credo Cube™ Series 22, 4 L Nested VIP available at pelicanbiothermal.com/products/credo-cube-series-22-41-nested-vip), with the inner box sitting on corner spacers within the outer box. The top and side gaps are 5.5 mm thick, while the bottom is approximately 4 mm thick. All surfaces allow for a bag approximately 200 mm×270 mm long to be placed between the boxes.

The top and side gaps each contain approximately 310 g of PCM, while the bottom contains 280 g. The PCM is contained within FoodSaver bags (FoodSaver® 8"×20' Vacuum-Seal Roll), and are sealed within a chamber vacuum sealer (VacMaster VP210). An impulse sealer has also been used.

Assembly: During initial assembly, bulk PCM is melted by warming to 65° C. in an incubator. The PCM was weighed into the bags, then the bags were sealed. The 280 g bag was placed between the bottom corner spacers, then the inner box was placed. Four bags containing 310 g of PCM were worked into the side gaps. An independent temperature/Humidity logger was placed inside the inner box. The last bag was attached to the outside surface of lid of the inner box. The upper corner cube spacers were placed, centering the inner box within the outer box. The outer lid was placed, and the outer shipping wrapper closed. The entire box and another temperature logger were then placed into a refrigerator at 12° C. to allow the PCM to cool and freeze in place.

Recording While Cooling: The inner box had already been fitted with temperature control electronics and fresh batteries. The 6 walls, PCM (top), and exterior (top) temperatures are monitored and recorded. The exterior temperature is somewhat isolated from the true exterior by the lightly insulating shipping wrapper, but still provides a reasonable indication of the environment.

The temperature control setpoint was set to 5° C., and the box started. This allows recording thermal performance without actually controlling the temperature (i.e. Passive mode). (See FIG. 27) Measurements are recorded every 5 minutes for 94 hours. The box was removed from the refrigerator at 20 Hours to check on its status.

Passive Temperature Cycle: Once the PCM was confirmed frozen, the box was run through a passive temperature cycle. The box was placed back into the 65° C. incubator for 48 Hr, then moved to the 10° C. refrigerator. Data from the box log (FIG. 29), and independent payload and external loggers was captured.

Active Temperature Cycle: The box temperature setpoint was raised from 5 C to its final target of 37 C. The same temperature cycle as before was started, with the intention to allow for a longer cooldown period. As the box has enough memory for 94 Hr, a warm-up for 48 hours would not allow for recording a cooldown for longer than 46 Hr. The box was read out at the end of the warm-up period, when a system fault was discovered.

Warm-Up and Low Battery: See FIG. 31. For the first 3 hours, the box recorded a low battery status (ERROR), suggesting the D-cell batteries were depleted. The box automatically acted to disable heating while this status existed. As soon as heating was disabled, the battery voltage (Vmin) recovered, and heating resumed. The low battery status then reoccurred. During this time, heating power indicated 0% (Pavg, heaters off). The details of this cycling are not available, but heating did occur as the payload temperature (Tavg) was always higher than the PCM temperature (Tpcm), and rising even faster.

As the payload temperature rose to near 37° C., the demand for heating was reduced. This allowed normal heater operation to resume for the rest of the test.

Battery Contact: The fault was traced to a high resistance battery contact to one of the D-cells. The spacer at the lower end of the cell was too thick to allow good reliable contact between the cell and the spring contact of the holder. The spacer thickness has been reduced from 3 mm to 2 mm. This will allow the cell to shift vertically in its holder slightly more than before, but still prevents the cell from over-compressing and deforming either spring contact. The thicker, upper contact spacer is unchanged.

Normal Operation: Once the Low Battery Fault cleared, normal box operation resumed. The payload temperature was held to 37±0.5° C. for over 18 hours, even after the PCM temperature had risen above 37° C. (the VIP is very effective at delaying temperature changes). The minimum battery voltage behaved as appropriate for the heating power demand. Normally, the box heats from 25° C. to 37° C. in about 90 minutes. If the battery contact issue had not occurred, payload temperature control for additional time may be possible.

Cool-down: The battery contact was sufficiently addressed for the remainder of this test by bending the lower contact to extend approximately 1 mm beyond the surface of the spacer. Box operation was completely normal following this correction (see FIG. 32).

Example 3: Radiological Incident

An application of the systems and methods provided herein are associated with an adverse incident, such as a radiological incident. There is a well-characterized impact of radiation on a living individual, including a human, with treatment and outcome dependent on the radiation dose. The challenge with a radiation event, of course, is understanding individual-by-individual, the actual radiation dose received as in an unexpected event, the impacted population are not wearing dosimeters. Accordingly, it is necessary to perform bioassays on each person's estimate radiation dose, such as whole-body or to specific organs. With those results, tailored treatment or palliative care can be administered. The challenges with collecting, handling and timely processing the samples and benefit of the instant system and methods are apparent.

FIG. 33 summarizes the steps required in order to tailor treatment to an individual impacted by the radiological incident 300, noting that depending on the particulars of the event, upwards of one million or more individuals could be impacted, with a corresponding number of samples. After sample collection 310 the sample is transported 320 to arrive at a facility (e.g. a lab) 330. At the lab, the samples are unpacked and processed so that a desired assay with corresponding results determined 340. The results are then communicated to appropriated personal for corresponding treatment of the impacted individuals, as indicated by arrow 360. Specific challenges include sample collection that is high quality blood sample for on the order of 1 million people and a long response time. With respect to the instant methods and devices, a challenge is the long response time 370 of the gold standard cytogenetic assay logistics, of up to about a week, associated with shipping 320, lab handling 330 and cell culture 340. See also FIG. 35, illustrating an about 1 week turn-around time for analytical biodosimetry with conventional shipping/processing, and the instant in-transit pre-processing, such as addition of reagents and a centrifugal in-transit processing step.

FIG. 34 summarizes the potential time savings by incorporating the methods and devices provided herein after a large scale nuclear/radiological event. The first smart shipping box (SSB) configuration, designed for national stockpiling, uses panels of printed circuit boards (PCBs) with a microcontroller (µC) and D-cell Alkaline batteries to generate a 37° C. environment within a traditional, insulated shipping box for blood cell culture. A customized proportional-integral-derivative (PID) control loop with pulse-width-modulation (PWM) was used to maintain temperature variation within 0.5° C. for accurate assay result. The µC-SSB was tested by shipping blood samples between Phoenix, Ariz., and New York City, N.Y. The CBMN micronucleus yields using the µC-SSB were similar to those using a laboratory incubator.

The second configuration comprises a centrifugal system (c-SSB) that can add Cytochalasin B (cyto-B) through a microfluidic capillary tip during shipment for the CBMN biodosimetry assay to make sure addition of cyto-B is within a critical time window of 24 to 44 hours. Correct centrifugal force and tip size for releasing cyto-B were selected based on possible mechanical shocks during transportation. Similar CBMN dose curves were also demonstrated between c-SSB with automatic cyto-B and laboratory incubator with manual cyto-B addition.

A centrifugal system within a shipping incubator is provided. The centrifuge is battery-powered, such as by a 12 V battery pack. Convection, such as by a fan, is used to obtain uniform temperature. A magnet is used to measure spin (rpm) speed. A cap may be molded, such as from PDMS, around a coated capillary tube, with reagent (e.g., cyto-B) at one end of the capillary and the other end available to the sample, such as an irradiated blood sample. This further demonstrates the feasibility of introducing a chemical reagent to the sample during transit.

Pre-processing shipping box and transportation are studies, including about 57.5 hours of 37° C. and in a fridge (about 5° C.) with 4 D cell alkaline batteries, with an attendant temperature variation that is less than plus/minus 0.2° C. (see, e.g., FIGS. 3-5). Additional sensors are utilized, including an accelerometer and two ShockWatch® indictors (25 g and 50 g), to monitor magnitude of shock.

The tests indicate that there are good binucleated cells and an appropriate dose-response curve of micronuclei per binucleated cells, with a correlation between lab and shipping incubators. FIG. 35A-35B illustrates the similarities between incubation in the container ("regular box") and 37° C. incubator in terms of average number of binucleated cells (top panel) and micronuclei/binucleated cell as a function of dose (Gy). FIG. 36 is a dose (Gy) versus MoN/BM of irradiated blood samples for storage in a $CO_2$ incubator and an instant "smart" storage container, further illustrating good agreement.

Any of the methods and devices may include data logging for the storage container, including external temperature, power utilized, battery life, temperature(s) (including for each of a plurality of temperature sensors), forces and component (e.g., connections, battery, tilt, shock) status.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preprocessing a biological sample during transit, the method comprising the steps of:
    storing a biological sample in a storage container having walls that define a storage volume;
    transporting the storage container with the stored biological sample to a sample processing facility;
    controlling one or more storage container parameters during the transporting step to initiate preprocessing of the biological sample;
    wherein the controlling step improves a biological sample processing parameter at the sample processing facility;
    wherein the one or more controlled storage container parameters is one or more of: temperature, reagent introduction, fixative introduction, centrifugation, mixing, washing, isolation, separation of one or more sample constituents, liquid manipulation, gas manipulation, or environmental control;
    wherein the transporting step begins at a location different than the sample processing facility, such that the transporting step occurs in a separate location than the sample processing facility; and
    wherein preprocessing refers to a processing of the sample during transit, that does not occur in the sample processing facility, such as chemical application, incubation, temperature cycling, physical separation or cell culturing, and wherein the preprocessing results in a reduction of time required at the sample processing facility.

2. The method of claim 1, wherein the improved biological sample processing parameter is one or more of:
a decrease in a number of processing steps at the sample processing facility;
a decrease in a processing time required at the sample processing facility upon delivery of the biological sample to the sample processing facility; or
an improved integrity of the sample processing outcome.

3. The method of claim 1, further comprising the step of sensing a storage container parameter during the transporting step with one or more sensors.

4. The method of claim 1, further comprising the step of collecting the biological sample, wherein the biological sample comprises a body fluid sample, a tissue sample, or an environmental sample.

5. The method of claim 1, wherein the biological sample is used in an assay selected from the group consisting of: a radiological exposure assay; a cancer assay; a chemical assay; a biothreat exposure assay; a diagnostic assay; a molecular imaging assay; and a spectroscopic assay.

6. The method of claim 1, further comprising the step of culturing cells in the biological sample during transport.

7. The method of claim 1, wherein the controlled storage container parameters vary over time during the transporting step.

8. The method of claim 1, wherein the storage container is vacuum-insulated comprising a plurality of sensors and actuators for controlling temperature in the storage container.

9. The method of claim 1, wherein the storage container comprises:
a plurality of sensors selected from the group consisting of: a temperature sensor, an accelerometer; a position (GPS) sensor, a time sensor, a humidity sensor, a mechanical shock sensor, a tilt sensor, a radiation sensor, an optical sensor, a magnetic sensor, and any combinations thereof; and
a plurality of actuators selected from the group consisting of: a thermal actuator, a fluidic actuator, a mechanical actuator, an optical actuator, an electronic actuator, and any combinations thereof.

10. The method of claim 1, wherein the storage container walls correspond to six surfaces, wherein a thermal actuator and a temperature sensor is connected to each surface, and a tethered temperature sensor is connected to the storage container to measure a container volume temperature or an external environmental temperature.

11. The method of claim 1, wherein the storage container comprises temperature sensors and thermal actuators that provide a steady-state temperature control of between 1° C. and 100° C. with a steady state temperature deviation that is within ±0.5° C. of a selected steady-state temperature over the transporting step, including a user-selected time-varying steady-state temperature.

12. The method of claim 1, wherein the storage container comprises an energy source, optionally a primary cell and/or a secondary cell, to provide power and control of the one or more storage container parameters for a time period that is greater than 0.25 hours and less than 7 days.

13. The method of claim 1, wherein the storage container further comprises a wireless transmitter and a receiver for two-way communication with an external controller, the method further comprising the step of remotely controlling the one or more storage container parameters by sending from the external controller a control signal to the actuators.

14. The method of claim 1, further comprising the step of recording a time course of system parameters, wherein the system parameters are selected from the group consisting of storage container location, storage container orientation, an impact force on the storage container, thermal actuator power level, temperature sensor reading, and any combinations thereof.

15. The method of claim 1, wherein each of a plurality of thermal actuators are independently controlled to accommodate a spatially-varying thermal load over an external surface of the storage container.

16. The method of claim 1, further comprising the step of automatically actuating thermal actuators to maintain the storage container volume within a user-specified temperature range.

17. The method of claim 1, further comprising monitoring an operation parameter selected from the group consisting of: main battery voltage, power disconnect event due to impact, thermal actuator disabled due to battery depletion, and internal error.

18. The method of claim 1, wherein the transporting step comprises transporting the storage container by an aerial drone.

19. The method of claim 1, wherein the preprocessing comprises the addition of a reagent to the biological sample by a centrifugal system positioned in the storage volume.

* * * * *